(12) United States Patent
Omer et al.

(10) Patent No.: US 12,396,651 B2
(45) Date of Patent: Aug. 26, 2025

(54) SYSTEM AND METHOD FOR DETECTING CHANGES IN HUMAN TISSUES

(71) Applicant: Urologic Health Ltd., Or Yehuda (IL)

(72) Inventors: Noam Omer, Rosh-Haayin (IL); Adam Yaacov, Tel-Aviv (IL)

(73) Assignee: UROLOGIC HEALTH LTD., Or Yehuda (IL)

( * ) Notice: Subject to any disclaimer, the term of this patent is extended or adjusted under 35 U.S.C. 154(b) by 935 days.

(21) Appl. No.: 17/427,939

(22) PCT Filed: Jan. 7, 2020

(86) PCT No.: PCT/IL2020/050022
§ 371 (c)(1),
(2) Date: Aug. 3, 2021

(87) PCT Pub. No.: WO2020/161694
PCT Pub. Date: Aug. 13, 2020

(65) Prior Publication Data
US 2022/0047179 A1   Feb. 17, 2022

Related U.S. Application Data

(60) Provisional application No. 62/800,576, filed on Feb. 4, 2019.

(51) Int. Cl.
*A61B 5/0536* (2021.01)
*A61B 5/00* (2006.01)
*A61B 5/25* (2021.01)

(52) U.S. Cl.
CPC .............. *A61B 5/0536* (2013.01); *A61B 5/25* (2021.01); *A61B 5/4343* (2013.01); *A61B 5/746* (2013.01)

(58) Field of Classification Search
CPC ....... A61B 5/0536; A61B 5/25; A61B 5/4343; A61B 5/746; A61B 5/00–7495
See application file for complete search history.

(56) References Cited

U.S. PATENT DOCUMENTS 6,236,886 B1   5/2001  Cherepenin et al.
6,330,470 B1  12/2001  Tucker et al.
(Continued)

FOREIGN PATENT DOCUMENTS

CN    105243267    1/2016
CN    106264462    1/2017
(Continued)

OTHER PUBLICATIONS

Pahuja, S.K., Anand, S. and Sengupta, A., 2011—Electrical Impedance Tomography Based Image Reconstruction and Feto-Maternal Monitoring in Pregnancy. Health, 3(08), p. 482.
(Continued)

*Primary Examiner* — Tse W Chen
*Assistant Examiner* — Evelyn Grace Park
(74) *Attorney, Agent, or Firm* — S. J. Intellectual Property Limited

(57) ABSTRACT

A system for non-invasively detecting changes in human tissues, the system comprising: an Electrical Impedance Tomography (EIT) sensor capable of acquiring readings associated with a group of human tissues of a patient; and a processing resource configured to: obtain reference state information based on a reference EIT reading obtained at a past time, the reference state information being indicative of a reference state of the group of human tissues; acquire, using the EIT sensor, a current reading; analyze the current EIT reading to determine current state information indicative of a current state of the group of human tissues; compare the reference state information with the current state infor-
(Continued)

mation to determine a change between the reference state of the group of human tissues and the current state of the group of human tissues; and provide output indicative of the change, or lack thereof, to a user of the system.

20 Claims, 5 Drawing Sheets

(56) References Cited

U.S. PATENT DOCUMENTS

| | | |
|---|---|---|
| 7,435,226 B2 | 10/2008 | Suarez |
| 7,499,745 B2 | 3/2009 | Littrup et al. |
| 7,896,814 B2 | 3/2011 | Teschner et al. |
| 7,907,998 B2 | 3/2011 | Arad (Abboud) |
| 10,602,973 B2 | 3/2020 | Loughney et al. |
| 2002/0106681 A1 | 8/2002 | Wexler et al. |
| 2003/0216663 A1* | 11/2003 | Jersey-Willuhn ...... A61B 5/412 |
| | | 977/932 |
| 2005/0107719 A1 | 5/2005 | Arad (Abbound) |
| 2005/0283058 A1 | 12/2005 | Choo-Smith et al. |
| 2013/0118736 A1 | 5/2013 | Usadi et al. |
| 2013/0197324 A1 | 8/2013 | Waterhouse et al. |
| 2013/0281861 A1* | 10/2013 | Flomerfelt ............... A61B 8/02 |
| | | 600/483 |
| 2016/0007879 A1 | 1/2016 | Gonzalez et al. |
| 2016/0242673 A1 | 8/2016 | Grychtol et al. |
| 2019/0038213 A1 | 2/2019 | Arad (Abboud) et al. |

FOREIGN PATENT DOCUMENTS

| | | |
|---|---|---|
| CN | 106845063 | 6/2017 |
| CN | 115311227 A | 11/2022 |
| WO | 2014191991 | 12/2014 |
| WO | 2017207972 | 12/2017 |

OTHER PUBLICATIONS

Pahuja, S.K. and Anand, S., 2010—Electrical Impedance Tomography Based Image Reconstruction of the Uterus Using Phantom. International Journal of Advanced Research in Computer Science, 1(1).

Gandhi, S.V., Walker, D.C., Brown, B.H. and Anumba, D.O., 2006—Comparison of Human Uterine Cervical Electrical Impedance Measurements Derived Using Two Tetrapolar Probes of Different Sizes. Biomedical Engineering Online, 5(1), p. 62.

* cited by examiner

SYSTEM AND METHOD FOR DETECTING CHANGES IN HUMAN TISSUES

TECHNICAL FIELD

The invention relates to the field of Electrical Impedance Tomography (EIT), and more specifically to a system and method for detecting changes in human tissues using EIT.

BACKGROUND

The human body is comprised of many types of human tissues, including muscle tissues, epithelial tissues, connective tissues and nervous tissues. At least some of the human tissues change over time, due to a negative process (e.g. illness, injury, decay, or any other cause), or due to a positive process (e.g. healing, recovery). Current solutions for detecting changes to human tissues are cumbersome, and require highly skilled personnel as well as expensive equipment whose operation requires training. Having the ability to detect changes in human tissues in a non-invasive and simple manner is clearly beneficial, both for patients and for medical practitioners. Changes may be indicative of hazardous situations, and in some cases, detecting the changes is critical for survival of the patient.

Vaginal Birth After Cesarean (VBAC) is a specific example, illustrating the importance of detecting changes in human tissues. After a cesarean section (also referred to herein as "C-section" or "cesarean surgery" interchangeably) performed on a patient to deliver a baby, a C-section scar is formed, extending from the uterus to the skin surface of the patient. During a vaginal birth attempt of a patient having a C-section scar, forces, excreted on the scar, increase its tension and may cause it to rupture. Uterine scar rupture during labor, or during Trial of Labor After Cesarean (TOLAC), may lead to uterus bleeding, fetal distress, fetus and/or placenta drop into the abdominal cavity, and it in turn may lead to a need in performance of an emergency cesarean surgery, stitching of the uterus and in some cases even hysterectomy. Uterine scar rupture during labor is clearly a dangerous phenomenon that occurs at about 0.5%-1% of the VBACs.

Due to the fact that there is a short time window to identify the C-section scar rupture before irreversible maternal and fetal damage is caused, using complicated imaging systems (such as ultrasound) that require long processing times is irrelevant. In addition, such systems are operated by designated professionals, and those professionals, as well as those imaging systems, are not available for every patient undergoing VBAC. Therefore, C-section scar rupture is currently diagnosed based on standard signs and symptoms, such as fetus heart rate irregularities, Fetus bradycardia, uterine tachysystole, intrauterine pressure decreases, uterine contraction stop, abdomen pain, vaginal bleeding, etc. However, such diagnosis methods are inaccurate, provide posteriori indications, after irreversible damage is already done, and thus cannot be compared to a direct detection of changes to the C-section scar that are indicative of a risk of it rupturing, or indicative of it being raptured.

The lack of suitable indications of the state of the C-section scar may result in a decision to unnecessarily operate and shift the labor process into a repeat caesarean section, or in a misdetection that could endanger the patient and\or the fetus.

There is thus a need in the art for a new method and system for detecting changes in human tissues.

References considered to be relevant as background to the presently disclosed subject matter are listed below. Acknowledgement of the references herein is not to be inferred as meaning that these are in any way relevant to the patentability of the presently disclosed subject matter.

US Patent application No. 2013/0197324 (Waterhouse et al.) published on Aug. 1, 2013 discloses a system and method of acquiring and transmitting uterine EMG signals is disclosed, where a signal processing module processes incoming uterine EMU signals from a patient and wirelessly transmits a processed signal to an information relaying device. The information relaying device is then configured to download the processed signal and transmit the signal to a call center or health care facility for physician evaluation. The system is ambulatory, thus allowing the patient to record and transmit uterine EMG signals anywhere a satisfactory transmission may be made. Additionally, a system and method of using electromyography for monitoring and diagnosis of uterine rupturing is disclosed, where incoming electrical signals from the lower uterine segment muscle fibers demonstrate an attenuated signal as the lower uterine segment thins and separates during the dilatation and effacement process of labor identifying those patients at increased risk for rupture.

Pahuja, S. K., Anand, S. and Sengupta, A., 2011 "Electrical Impedance Tomography Based Image Reconstruction and Feto-Maternal Monitoring In Pregnancy", Health, 3(08), P.482 discloses standard methods of monitoring the fetus and maternal health during labor are cardioto-cogram, tocography, ultrasound and magneto-cardiograpghy. These methods have some limitations in real time continuous monitoring and cause some degree of inconvenience to the patient and demand special attendance of the obstetrician also these methods cannot be used for continuous monitoring of the fetal well-being. To overcome the limitations of above techniques, a non-invasive bioimpedance measuring method is proposed. This technique helps in monitoring and recording of the electrical field distribution of a closed object. The output variation on the outer surface is likely to provide information because of fetal movements and related to physiological parameters. It will also help in the development of Electrical Impedance Tomography based imaging technique for a closed body system with special reference to fetal monitoring in-utero during pregnancy and labor.

Pahuja, S. K. and Anand, S., 2010 "Electrical Impedance Tomography Based Image Reconstruction of The Uterus Using Phantom", International Journal of Advanced Research in Computer Science, 1(1) discloses the resistivity of different human tissue varies with large difference ranging from cerebrosinal fluid to bone. Images of such varied distributed resistivities inside a closed object can easily be reconstructed using image reconstruction algorithm. Electrical impedance tomography is relatively a new imaging technique which maps the distribution of electric resistivity of the closed object such as our body. The aim is to reconstruct a conductivity image in the phantom papaya which is a model of a uterus of human using finite element method.

Gandhi, S. V., Walker, D. C., Brown, B. H. and Anumba, D. O., 2006 "Comparison Of Human Uterine Cervical Electrical Impedance Measurements Derived Using Two Tetrapolar Probes of Different Sizes", Biomedical Engineering Online, 5(1), P.62 discloses comparing uterine cervical electrical impedance spectroscopy measurements employing two probes of different sizes, and employing a finite element model to predict and compare the fraction of electrical current derived from subepithelial stromal tissue.

Methods: Cervical impedance was measured in 12 subjects during early pregnancy using 2 different sizes of the probes on each subject. Results: Mean cervical resistivity was significantly higher (5.4 vs. 2.8 ΩM; p<0.001) with the smaller probe in the frequency rage of 4-819 kHz. There was no difference in the short-term intraobserver variability between the two probes. The cervical impedance measurements derived in vivo followed the pattern predicted by the finite element model. Conclusion: Inter-electrode distance on the probes for measuring cervical impedance influences the tissue resistivity values obtained. Determining the appropriate probe size is necessary when conducting clinical studies of resistivity of the cervix and other human tissues.

Chinese Patent application No. 106264462 (Qiuping et at), published on Jan. 4, 2017 discloses a method for predicting re-pregnant vaginal birth after cesarean delivery. The method comprises the following steps: S1: collecting a large number of clinical data of pregnant and lying-in women experiencing re-pregnant trial vaginal birth after cesarean delivery; S2: comparing the clinical data of two groups of pregnant and lying-in women, screening independent influence factors for influencing successful re-pregnant trial vaginal birth after cesarean delivery, and calculating an odds ratio (OR) of each influence factor; S3: grading and classifying the independent influence factors, scoring the obtained odds ratios (OR) in combination with logistic regression analysis so as to establish a predictive scoring table used before the re-pregnant VBACdelivery; S4: according to the predictive scoring table, scoring the collected independent influence factors of each pregnant and lying-in woman, calculating a total score value, and drawing the total score values of all the pregnant and lying-in women into an ROC (receiver operating characteristic) curve to obtain an optimal critical score value, namely a cut-off point, wherein the cut-off point is a critical score value for judging whether a pregnant woman can accomplish the vaginal birth. By the method, a safe and feasible before-birth predictive scoring model for VBAC is established.

Chinese Patent application No. 106845063 (Jing et al.) published on Jun. 13, 2017 discloses a method and a system for predicting the success rate of delivery of a scar uterine. The method comprises the steps of: carrying out basic data collection and registration on a pregnant, woman who is enrolled in the hospital, wherein the basic data comprises age, height, the pre-pregnancy BMI, the BMI in hospital, and the history record of vaginal delivery; collecting cervix maturity parameters of the pregnant woman who is enrolled in the hospital, wherein the cervix maturity parameters comprise the degree of dilation of the cervix and the degree of disappearance of the cervical canals; and taking the collected parameters as input parameters to input into a trained mathematical prediction model for calculation, and finally obtaining the success rate of vaginal delivery of the pregnant woman.

Chinese Patent application No. 105243267 (Yanjie et al.) published on Jan. 13, 2016 discloses a method for predicting the success rate of scarred uterus trial-production. The method comprises: collecting data of a pregnant woman, including antepartum parity, an antepartum BMI (Body Mass Index), a cervix prenatal situation, and whether PROM (premature rupture of membranes) occurs or not; performing calculation by using $P=1/[1/+exp(-0.785+1.3259\times1-1.5061\times2-1.2449\times31-1.4211\times32+0.7616\times4)]*100\%$; and predicting the success rate of the pregnant woman uterus trial-production according to a P value, so as to provide a reference index for the pregnant woman and doctors. The method is easy in data collection, high in prediction success rate, and especially suitable for vagina trial-production prediction of Chinese pregnant women with a scarred uterus.

General Description

In accordance with a first aspect of the presently disclosed subject matter, there is provided a system for non-invasively detecting changes in human tissues, the system comprising: an Electrical Impedance Tomography (EIT) sensor capable of acquiring readings associated with a group of human tissues of a patient; and a processing resource configured to: (a) obtain reference state information based on a reference EIT reading obtained at a past time, the reference state information being indicative of a reference state of the group of human tissues; (b) acquire, using the EIT sensor, a current EIT reading; (c) analyze the current EIT reading to determine current state information indicative of a current state of the group of human tissues; (d) compare the reference state information with the current state information to determine a change between the reference state of the group of human tissues and the current state of the group of human tissues; and (e) provide output indicative of the change, or lack thereof, to a user of the system.

In some cases, (a) the EIT sensor comprises at least four non-invasive electrodes, (b) the current EIT reading includes a series of one or more subsequent projections, each of the projections obtained by: at least one pair of the non-invasive electrodes transmitting electrical current from a first electrode of the pair to a second electrode of the pair, and at least one other pair of other non-invasive electrodes of the non-invasive electrodes measuring an electrical potential between a first electrode of the other pair and a second electrode of the other pair simultaneously to the transmitting, wherein the pair and the other pair include different non-invasive electrodes at each projection of the series, and (c) upon the non-invasive electrodes being positioned around an area of interest comprising the group of human tissues of the patient, the at least part of the measured electrical potential is affected by at least part of the group of human tissues.

In some cases, the projections of the series are performed in synchronization with a breathing cycle of the patient.

In some cases, the group of human tissues comprises at least part of one of the following: a scar, one or more blood vessels, one or more teeth, transplanted skin, a brain.

In some cases, the scar is a cesarean section scar, the change is a deformation of the scar, and the output includes an alert when based on the deformation of the scar the likelihood of the scar to rupture is above a first threshold.

In some cases, the processing resource is further configured to iteratively repeat steps (a)-(e) at a plurality of different times.

In some cases, at each given iteration of the iterations the reference state information is the current state information of one or more previous iterations performed before the given iteration.

In some cases, the plurality of different times are during labor of the patient having the cesarean section scar.

In some cases, the processing resource is further configured to provide a second alert indicative of the change to the user of the system when based on the deformation of the scar the likelihood of the scar to rupture is above a second threshold, higher than the first threshold.

In some cases, the change is one of: recovery of the scar, recovery of the blood vessels, recovery of transplanted skin, recovery of the brain.

In some cases, the change is a cavity in one or more of the teeth.

In some cases, the output includes a visual map of an area comprising the group of human tissues, the visual map being indicative of the change.

In some cases, at least one of the reference state information or the current state information is a calculated parameter, calculated utilizing the reference reading or the current EIT reading, respectively.

In some cases, at least one of the reference state information or the current state information is the reference EIT reading itself or the current EIT reading itself, respectively.

In some cases, the series is defined by a scheme, and wherein the scheme further defines, for each projection of the series, a frequency of the electrical current transmitted by each of the first electrodes to each of the second electrodes of each of the pairs.

In some cases, the frequency transmitted from the first electrode to the second electrode of a first pair of the pairs is different than the frequency transmitted from the first electrode to the second electrode of a second pair of the pairs.

In some cases, the frequency transmitted from the first electrode to the second electrode of a given pair of the pairs in a first projection of the series is different than the frequency transmitted from the first electrode to the second electrode of the given pair in a second projection of the series other than the first projection.

In some cases: (a) the EIT sensor further comprises at least four additional non-invasive electrodes, (b) each of the projections further obtained by: at least one third pair of the additional non-invasive electrodes transmitting electrical current from a first electrode of the third pair to a second electrode of the third pair, and at least one fourth pair of other additional non-invasive electrodes of the additional non-invasive electrodes measuring a second electrical potential between a first electrode of the fourth pair and a second electrode of the fourth pair simultaneously to the transmitting, wherein the third pair and the fourth pair include different additional non-invasive electrodes at each projection of the series, and (c) upon the additional non-invasive electrodes being positioned around an area of interest not comprising the group of human tissues of the patient, the second electrical potential measured is not affected by the group of human tissues.

In some cases, the analysis includes utilizing the second electrical potential that is not affected by the group of human tissues for filtering noise from the electrical potential is affected by at least part of the group of human tissues.

In accordance with a second aspect of the presently disclosed subject matter, there is provided a system for non-invasively monitoring a cesarean section scar of a patient during labor, the system comprising: an Electrical Impedance Tomography (EIT) sensor capable of acquiring readings associated with the cesarean section scar of the patient; and a processing resource configured to: (a) obtain reference state information based on a reference EIT reading obtained at a past time, the reference state information being indicative of a reference state of the cesarean section scar; (b) acquire, using the EIT sensor, a current EIT reading; (c) analyze the current EIT reading to determine current state information indicative of a current state of the cesarean section scar; (d) compare the reference state information with the current state information to determine a change between the reference state of the cesarean section scar and the current state of the cesarean section scar; and (e) upon the change meeting a rule, provide an alert to a user of the system, indicative of a risk of the cesarean section scar rapturing.

In accordance with a third aspect of the presently disclosed subject matter, there is provided a system for non-invasively classifying stages of a physiological process associated with human tissues, the system comprising: an Electrical Impedance Tomography (EIT) sensor capable of acquiring readings associated with a group of human tissues of a patient; and a processing resource configured to: (a) obtain a classifier, the classifier configured to classify input into one of a plurality of reference states of the group of human tissues, each reference state being associated with a corresponding stage of a physiological process taking place, wherein the physiological process affects the group of human tissues; (b) acquire, using the EIT sensor, a current EIT reading; (c) analyze the current HT reading to determine current state information indicative of a current state of the group of human tissues; (d) classify the current state information using the classifier to determine a current stage of the physiological process; and (e) provide output indicative of the current stage of the physiological process, to a user of the system.

In some cases, the classifier is generated by performing machine learning on a training set of pre-classified training EIT readings.

In some cases, the pre-classified training EIT readings are obtained by supervised simulation.

In some cases:) the EIT sensor comprises at least four non-invasive electrodes, (b) the current EIT reading includes a series of one or more subsequent projections, each of the projections obtained by: at least one pair of the non-invasive electrodes transmitting electrical current from a first electrode of the pair to a second electrode of the pair, and at least one other pair of other non-invasive electrodes of the non-invasive electrodes measuring an electrical potential between a first electrode of the other pair and a second electrode of the other pair simultaneously to the transmitting, wherein the pair and the other pair include different non-invasive electrodes at each projection of the series, and (c) upon the non-invasive electrodes being positioned around an area of interest comprising the group of human tissues of the patient, the at least part of the measured electrical potential is affected by at least part of the group of human tissues.

In some cases, the projections of the series are performed in synchronization with a breathing cycle of the patient.

In some cases, the group of human tissues comprises at least part of one of the following: a scar, one or more blood vessels, one or more teeth, transplanted skin, a brain.

In some cases, the scar is a cesarean section scar, the physiological process is the cesarean section scar rupturing, and the output includes an alert when according to the stage of the physiological process the likelihood of the scar to rupture is above a threshold.

In some cases, the processing resource is further configured to iteratively repeat steps (a)-(e) at a plurality of different times.

In some cases, the plurality of different times are during labor of the patient having the cesarean section scar.

In some cases, the physiological process is one of: recovery of the scar, recovery of the blood vessels, recovery of transplanted skin, recovery of the brain.

In some cases, the physiological process is a formation of a cavity in one or more of the teeth.

In some cases, the current state information is a calculated parameter, calculated utilizing the current EIT reading.

In some cases, the current state information is the current EIT reading itself.

In some cases, the series is defined by a scheme, and wherein the scheme further defines, for each projection of the series, a frequency of the electrical current transmitted by each of the first electrodes to each of the second electrodes of each of the pairs.

In some cases, the frequency transmitted from the first electrode to the second electrode of a first pair of the pairs is different than the frequency transmitted from the first electrode to the second electrode of a second pair of the pairs.

In some cases, the frequency transmitted from the first electrode to the second electrode of a given pair of the pairs in a first projection of the series is different than the frequency transmitted from the first electrode to the second electrode of the given pair in a second projection of the series other than the first projection.

In some cases: (a) the EIT sensor further comprises at least four additional non-invasive electrodes, (b) each of the projections further obtained by: at least one third pair of the additional non-invasive electrodes transmitting electrical current from a first electrode of the third pair to a second electrode of the third pair, and at least one fourth pair of other additional non-invasive electrodes of the additional non-invasive electrodes measuring a second electrical potential between a first electrode of the fourth pair and a second electrode of the fourth pair simultaneously to the transmitting, wherein the third pair and the fourth pair include different additional non-invasive electrodes at each projection of the series, and (c) upon the additional non-invasive electrodes being positioned around an area of interest not comprising the group of human tissues of the patient, the second electrical potential measured is not affected by the group of human tissues.

In some cases, the analysis includes utilizing the second electrical potential that is not affected by the group of human tissues for filtering noise from the electrical potential that is affected by at least part of the group of human tissues.

In accordance with a fourth aspect of the presently disclosed subject matter, there is provided a system for non-invasively classifying stages of a physiological process associated with human tissues, the system comprising: an Electrical Impedance Tomography (EIT) sensor capable of acquiring readings associated with a group of human tissues of a patient; and a processing resource configured to: (a) acquire, using the EIT sensor, a current EIT reading; (b) solve, using a reconstruction algorithm, an inverse problem to identify parameters of a biological model corresponding to the current EIT reading, wherein the parameters are associated with a current state of the group of human tissues; (c) provide output to a user of the system, the output being (a) based on at least one of the parameters, or on a calculated parameter based on at least one of the parameters, and (b) indicative of the current stage of the physiological process.

In some cases: (a) the EIT sensor comprises at least four non-invasive electrodes, (b) the current EIT reading includes a series of one or more subsequent projections, each of the projections obtained by: at least one pair of the non-invasive electrodes transmitting electrical current from a first electrode of the pair to a second electrode of the pair, and at least one other pair of other non-invasive electrodes of the non-invasive electrodes measuring an electrical potential between a first electrode of the other pair and a second electrode of the other pair simultaneously to the transmitting, wherein the pair and the other pair include different non-invasive electrodes at each projection of the series, and (c) upon the non-invasive electrodes being positioned around an area of interest comprising the group of human tissues of the patient, the at least part of the measured electrical potential is affected by at least part of the group of human tissues.

In some cases, the projections of the series are performed in synchronization with a breathing cycle of the patient.

In some cases, the group of human tissues comprises at least part of one of the following: a scar, one or more blood vessels, one or more teeth, transplanted skin, a brain.

In some cases, the scar is a cesarean section scar, the physiological process is the cesarean section scar rupturing, and the output includes an alert when according to the stage of the physiological process the likelihood of the scar to rupture is above a threshold.

In some cases, the processing resource is further configured to iteratively repeat steps (a)-(c) at a plurality of different times.

In some cases, the plurality of different times are during labor of the patient having the cesarean section scar.

In some cases, the physiological process is one of: recovery of the scar, recovery of the blood vessels, recovery of transplanted skin, recovery of the brain.

In some cases, the physiological process is a formation of a cavity in one or more of the teeth.

In some cases, the series is defined by a scheme, and wherein the scheme further defines, for each projection of the series, a frequency of the electrical current transmitted by each of the first electrodes to each of the second electrodes of each of the pairs.

In some cases, the frequency transmitted from the first electrode to the second electrode of a first pair of the pairs is different than the frequency transmitted from the first electrode to the second electrode of a second pair of the pairs.

In some cases, the frequency transmitted from the first electrode to the second electrode of a given pair of the pairs in a first projection of the series is different than the frequency transmitted from the first electrode to the second electrode of the given pair in a second projection of the series other than the first projection.

In some cases: (a) the EIT sensor further comprises at least four additional non-invasive electrodes, (b) each of the projections further obtained by: at least one third pair of the additional non-invasive electrodes transmitting electrical current from a first electrode of the third pair to a second electrode of the third pair, and at least one fourth pair of other additional non-invasive electrodes of the additional non-invasive electrodes measuring a second electrical potential between a first electrode of the fourth pair and a second electrode of the fourth pair simultaneously to the transmitting, wherein the third pair and the fourth pair include different additional non-invasive electrodes at each projection of the series, and (c) upon the additional non-invasive electrodes being positioned around an area of interest not comprising the group of human tissues of the patient, the second electrical potential measured is not affected by the group of human tissues.

In some cases, the solve includes utilizing the second electrical potential that is not affected by the group of human tissues for filtering noise from the current EIT readings.

In accordance with a fifth aspect of the presently disclosed subject matter, there is provided a method for non-invasively detecting changes in human tissues, the method comprising: (a) obtaining reference state information based on a reference EIT reading obtained at a past time, the reference state information being indicative of a reference state of a group of human tissues of a patient; (b) acquiring, using an Electrical Impedance Tomography (EIT) sensor capable of acquiring readings associated with the group of human tissues, a current EIT reading; (c) analyzing the current EIT reading to determine current state information indicative of a current state of the group of human tissues; (d) comparing the reference state information with the current state information to determine a change between the reference state of the group of human tissues and the current state of the group of human tissues; and (e) providing output indicative of the change, or lack thereof, to a user.

In some cases: (a) the EIT sensor comprises at least four non-invasive electrodes, (b) the current EIT reading includes a series of one or more subsequent projections, each of the projections obtained by: at least one pair of the non-invasive electrodes transmitting electrical current from a first electrode of the pair to a second electrode of the pair, and at least one other pair of other non-invasive electrodes of the non-invasive electrodes measuring an electrical potential between a first electrode of the other pair and a second electrode of the other pair simultaneously to the transmitting, wherein the pair and the other pair include different non-invasive electrodes at each projection of the series, and (c) upon the non-invasive electrodes being positioned around an area of interest comprising the group of human tissues of the patient, the at least part of the measured electrical potential is affected by at least part of the group of human tissues.

In some cases, the projections of the series are performed in synchronization with a breathing cycle of the patient.

In some cases, the group of human tissues comprises at least part of one of the following: a scar, one or more blood vessels, one or more teeth, transplanted skin, a brain.

In some cases, the scar is a cesarean section scar, the change is a deformation of the scar, and the output includes an alert when based on the deformation of the scar the likelihood of the scar to rupture is above a first threshold.

In some cases, the method further comprises iteratively repeating steps (a)-(e) at a plurality of different times.

In some cases, at each given iteration of the iterations the reference state information is the current state information of one or more previous iterations performed before the given iteration.

In some cases, the plurality of different times are during labor of the patient having the cesarean section scar.

In some cases, the method further comprises providing a second alert indicative of the change to the user when based on the deformation of the scar the likelihood of the scar to rupture is above a second threshold, higher than the first threshold.

In some cases, the change is one of: recovery of the scar, recovery of the blood vessels, recovery of transplanted skin, recovery of the brain.

In some cases, the change is a cavity in one or more of the teeth.

In some cases, the output includes a visual map of an area comprising the group of human tissues, the visual map being indicative of the change.

In some cases, at least one of the reference state information or the current state information is a calculated parameter, calculated utilizing the reference EIT reading or the current EIT reading, respectively.

In some cases, at least one of the reference state information or the current state information is the reference EIT reading itself or the current EIT reading itself, respectively.

In some cases, the series is defined by a scheme, and wherein the scheme further defines, for each projection of the series, a frequency of the electrical current transmitted by each of the first electrodes to each of the second electrodes of each of the pairs.

In some cases, the frequency transmitted from the first electrode to the second electrode of a first pair of the pairs is different than the frequency transmitted from the first electrode to the second electrode of a second pair of the pairs.

In some cases, the frequency transmitted from the first electrode to the second electrode of a given pair of the pairs in a first projection of the series is different than the frequency transmitted from the first electrode to the second electrode of the given pair in a second projection of the series other than the first projection.

In some cases: (a) the EIT sensor further comprises at least four additional non-invasive electrodes, (b) each of the projections further obtained by: at least one third pair of the additional non-invasive electrodes transmitting electrical current from a first electrode of the third pair to a second electrode of the third pair, and at least one fourth pair of other additional non-invasive electrodes of the additional non-invasive electrodes measuring a second electrical potential between a first electrode of the fourth pair and a second electrode of the fourth pair simultaneously to the transmitting, wherein the third pair and the fourth pair include different additional non-invasive electrodes at each projection of the series, and (c) upon the additional non-invasive electrodes being positioned around an area of interest not comprising the group of human tissues of the patient, the second electrical potential measured is not affected by the group of human tissues.

In some cases, the analyzing includes utilizing the second electrical potential that is not affected by the group of human tissues for filtering noise from the electrical potential is affected by at least part of the group of human tissues.

In accordance with a sixth aspect of the presently disclosed subject matter, there is provided a method for non-invasively monitoring a cesarean section scar of a patient during labor, the method comprising: (a) obtaining reference state information based on a reference EIT reading obtained at a past time, the reference state information being indicative of a reference state of the cesarean section scar of the patient; (b) acquiring, using an Electrical Impedance Tomography (EIT) sensor capable of acquiring readings associated with the cesarean section scar of the patient, a current EIT reading; (c) analyzing the current EIT reading to determine current state information indicative of a current state of the cesarean section scar; (d) comparing the reference state information with the current state information to determine a change between the reference state of the cesarean section scar and the current state of the cesarean section scar; and (e) upon the change meeting a rule, providing an alert to a user, indicative of a risk of the cesarean section scar capturing.

In accordance with a seventh aspect of the presently disclosed subject matter, there is provided a method for non-invasively classifying stages of a physiological process associated with human tissues, the method comprising: (a) obtaining a classifier, the classifier configured to classify input into one of a plurality of reference states of a group of human tissues of a patient, each reference state being associated with a corresponding stage of a physiological process taking place, wherein the physiological process affects the group of human tissues; (b) acquiring, using an Electrical Impedance Tomography (EIT) sensor capable of acquiring readings associated with the group of human tissues of the patient, a current EIT reading; (c) analyzing the current EIT reading to determine current state information indicative of a current state of the group of human tissues; (d) classifying the current state information using the classifier to determine a current stage of the physiological process; and (e) providing output indicative of the current stage of the physiological process, to a user.

In some cases, the classifier is generated by performing machine learning on a training set of pre-classified training EIT readings.

In some cases, the pre-classified training EIT readings are obtained by supervised simulation.

In some cases: (a) the EIT sensor comprises at least four non-invasive electrodes, (b) the current EIT reading includes a series of one or more subsequent projections, each of the projections obtained by: at least one pair of the non-invasive electrodes transmitting electrical current from a first electrode of the pair to a second electrode of the pair, and at least one other pair of other non-invasive electrodes of the non-invasive electrodes measuring an electrical potential between a first electrode of the other pair and a second electrode of the other pair simultaneously to the transmitting, wherein the pair and the other pair include different non-invasive electrodes at each projection of the series, and (c) upon the non-invasive electrodes being positioned around an area of interest comprising the group of human tissues of the patient, the at least part of the measured electrical potential is affected by at least part of the group of human tissues.

In some cases, the projections of the series are performed in synchronization with a breathing cycle of the patient.

In some cases, the group of human tissues comprises at least part of one of the following: a scar, one or more blood vessels, one or more teeth, transplanted skin, a brain.

In some cases, the scar is a cesarean section scar, the physiological process is the cesarean section scar rupturing, and the output includes an alert when according to the stage of the physiological process the likelihood of the scar to rupture is above a threshold.

In some cases, the method further comprises iteratively repeating steps (a)-(e) at a plurality of different times.

In some cases, the plurality of different lines are during labor of the patient having the cesarean section scar.

In some cases, the physiological process is one of: recovery of the scar, recovery of the blood vessels, recovery of transplanted skin, recovery of the brain.

In some cases, the physiological process is a formation of a cavity in one or more of the teeth.

In some cases, the current state information is a calculated parameter, calculated utilizing the current EIT reading.

In some cases, the current state information is the current EIT reading itself.

In some cases, the series is defined by a scheme, and wherein the scheme further defines, for each projection of the series, a frequency of the electrical current transmitted by each of the first electrodes to each of the second electrodes of each of the pairs.

In some cases, the frequency transmitted from the first electrode to the second electrode of a first pair of the pairs is different than the frequency transmitted from the first electrode to the second electrode of a second pair of the pairs.

In some cases, the frequency transmitted from the first electrode to the second electrode of a given pair of the pairs in a first projection of the series is different than the frequency transmitted from the first electrode to the second electrode of the given pair in a second projection of the series other than the first projection.

In some cases: (a) the EIT sensor further comprises at least four additional non-invasive electrodes, (b) each of the projections further obtained by: at least one third pair of the additional non-invasive electrodes transmitting electrical current from a first electrode of the third pair to a second electrode of the third pair, and at least one fourth pair of other additional non-invasive electrodes of the additional non-invasive electrodes measuring a second electrical potential between a first electrode of the fourth pair and a second electrode of the fourth pair simultaneously to the transmitting, wherein the third pair and the fourth pair include different additional non-invasive electrodes at each projection of the series, and (c) upon the additional non-invasive electrodes being positioned around an area of interest not comprising the group of human tissues of the patient, the second electrical potential measured is not affected by the group of human tissues.

In some cases, the analyzing includes utilizing the second electrical potential that is not affected by the group of human tissues for filtering noise from the electrical potential that, is affected by at least part of the group of human tissues.

In accordance with an eighth aspect of the presently disclosed subject matter, there is provided a method for non-invasively classifying stages of a physiological process associated with human tissues, the method comprising: (a) acquiring, using an Electrical Impedance Tomography (EIT) sensor capable of acquiring readings associated with a group of human tissues of a patient, a current EIT reading; (b) solving, using a reconstruction algorithm, an inverse problem to identify parameters of a biological model corresponding to the current EIT reading, wherein the parameters are associated with a current state of the group of human tissues; (c) providing output to a user, the output being (aa) based on at least one of the parameters, or on a calculated parameter based on at least one of the parameters, and (bb) indicative of the current stage of the physiological process.

In some cases: (a) the EIT sensor comprises at least four non-invasive electrodes, (b) the current EIT reading includes a series of one or more subsequent projections, each of the projections obtained by: at least one pair of the non-invasive electrodes transmitting electrical current from a first electrode of the pair to a second electrode of the pair, and at least one other pair of other non-invasive electrodes of the non-invasive electrodes measuring an electrical potential between a first electrode of the other pair and a second electrode of the other pair simultaneously to the transmitting, wherein the pair and the other pair include different non-invasive electrodes at each projection of the series, and (c) upon the non-invasive electrodes being positioned around an area of interest comprising the group of human tissues of the patient, the at least part of the measured electrical potential is affected by at least part of the group of human tissues.

In some cases, the projections of the series are performed in synchronization with a breathing cycle of the patient.

In some cases, the group of human tissues comprises at least part of one of the following: a scar, one or more blood vessels, one or more teeth, transplanted skin, a brain.

In some cases, the scar is a cesarean section scar, the physiological process is the cesarean section scar rupturing, and the output includes an alert when according to the stage of the physiological process the likelihood of the scar to rupture is above a threshold.

In some cases, the method further comprises iteratively repeating steps (a)-(c) at a plurality of different times.

In some cases, the plurality of different times are during labor of the patient having the cesarean section scar.

In some cases, the physiological process is one of: recovery of the scar, recovery of the blood vessels, recovery of transplanted skin, recovery of the brain.

In some cases, the physiological process is a formation of a cavity in one or more of the teeth.

In some cases, the series is defined by a scheme, and wherein the scheme further defines, for each projection of the series, a frequency of the electrical current transmitted by each of the first electrodes to each of the second electrodes of each of the pairs.

In some cases, the frequency transmitted from the first electrode to the second electrode of a first pair of the pairs is different than the frequency transmitted from the first electrode to the second electrode of a second pair of the pairs.

In some cases, the frequency transmitted from the first electrode to the second electrode of a given pair of the pairs in a first projection of the series is different than the frequency transmitted from the first electrode to the second electrode of the given pair in a second projection of the series other than the first projection.

In some cases: (a) the EIT sensor further comprises at least four additional non-invasive electrodes, (b) each of the projections further obtained by: at least one third pair of the additional non-invasive electrodes transmitting electrical current from a first electrode of the third pair to a second electrode of the third pair, and at least one fourth pair of other additional non-invasive electrodes of the additional non-invasive electrodes measuring a second electrical potential between a first electrode of the fourth pair and a second electrode of the fourth pair simultaneously to the transmitting, wherein the third pair and the fourth pair include different additional non-invasive electrodes at each projection of the series, and (c) upon the additional non-invasive electrodes being positioned around an area of interest not comprising the group of human tissues of the patient, the second electrical potential measured is not affected by the group of human tissues.

In some cases, the solving includes utilizing the second electrical potential that is not affected by the group of human tissues for filtering noise from the current EIT readings.

In accordance with an ninth aspect of the presently disclosed subject matter, there is provided a non-transitory computer readable storage medium having computer readable program code embodied therewith, the computer readable program code, executable by a processing resource of a computer to perform a method for non-invasively detecting changes in human tissues, the method comprising: (a) obtaining reference state information based on a reference EIT reading obtained at a past time, the reference state information being indicative of a reference state of a group of human tissues of a patient; (b) acquiring, using an Electrical Impedance Tomography (EIT) sensor capable of acquiring readings associated with the group of human tissues, a current EIT reading; (c) analyzing the current EIT reading to determine current state information indicative of a current state of the group of human tissues; (d) comparing the reference state information with the current state information to determine a change between the reference state of the group of human tissues and the current state of the group of human tissues; and (e) providing output indicative of the change, or lack thereof, to a user.

In accordance with an tenth aspect of the presently disclosed subject matter, there is provided a non-transitory computer readable storage medium having computer readable program code embodied therewith, the computer readable program code, executable by a processing resource of a computer to perform a method for non-invasively monitoring a cesarean section scar of a patient during labor, the method comprising: (a) obtaining reference state information based on a reference EIT reading obtained at a past time, the reference state information being indicative of a reference state of the cesarean section scar of the patient; (b) acquiring, using an Electrical Impedance Tomography (EIT) sensor capable of acquiring readings associated with the cesarean section scar of the patient, a current EIT reading; (c) analyzing the current EIT reading to determine current state information indicative of a current state of the cesarean section scar; (d) comparing the reference state information with the current state information to determine a change between the reference state of the cesarean section scar and the current state of the cesarean section scar; and (e) upon the change meeting a rule, providing an alert to a user, indicative of a risk of the cesarean section scar rupturing.

In accordance with an eleventh aspect of the presently disclosed subject matter, there is provided a non-transitory computer readable storage medium having computer readable program code embodied therewith, the computer readable program code, executable by a processing resource of a computer to perform a method for non-invasively classifying stages of a physiological process associated with human tissues, the method comprising: (a) obtaining a classifier, the classifier configured to classify input into one of a plurality of reference states of a group of human tissues of a patient, each reference state being associated with a corresponding stage of a physiological process taking place, wherein the physiological process affects the group of human tissues; (b) acquiring, using an Electrical Impedance Tomography (EIT) sensor capable of acquiring readings associated with the group of human tissues of the patient, a current EIT reading; (c) analyzing the current EIT reading to determine current state information indicative of a current state of the group of human tissues; (d) classifying the current state information using the classifier to determine a current stage of the physiological process; and (e) providing output indicative of the current stage of the physiological process, to a user.

In accordance with an twelfth aspect of the presently disclosed subject matter, there is provided a non-transitory computer readable storage medium having computer readable program code embodied therewith, the computer readable program code, executable by a processing resource of a computer to perform a method for non-invasively classifying stages of a physiological process associated with human tissues, the method comprising: (a) acquiring, using an Electrical Impedance Tomography (EIT) sensor capable of acquiring readings associated with a group of human tissues of a patient, a current EIT reading; (b) solving, using a reconstruction algorithm, an inverse problem to identify parameters of a biological model corresponding to the current EIT reading, wherein the parameters are associated with a current state of the group of human tissues; (c) providing output to a user, the output being (aa) based on at least one of the parameters, Or Oil a calculated parameter based on at least one of the parameters, and (bb) indicative of the current stage of the physiological process.

BRIEF DESCRIPTION OF THE DRAWINGS

In order to understand the presently disclosed subject matter and to see how it may be carried out in practice, the subject matter will now be described, by way of non-limiting examples only, with reference to the accompanying drawings, in which.

DETAILED DESCRIPTION

Figure 1:
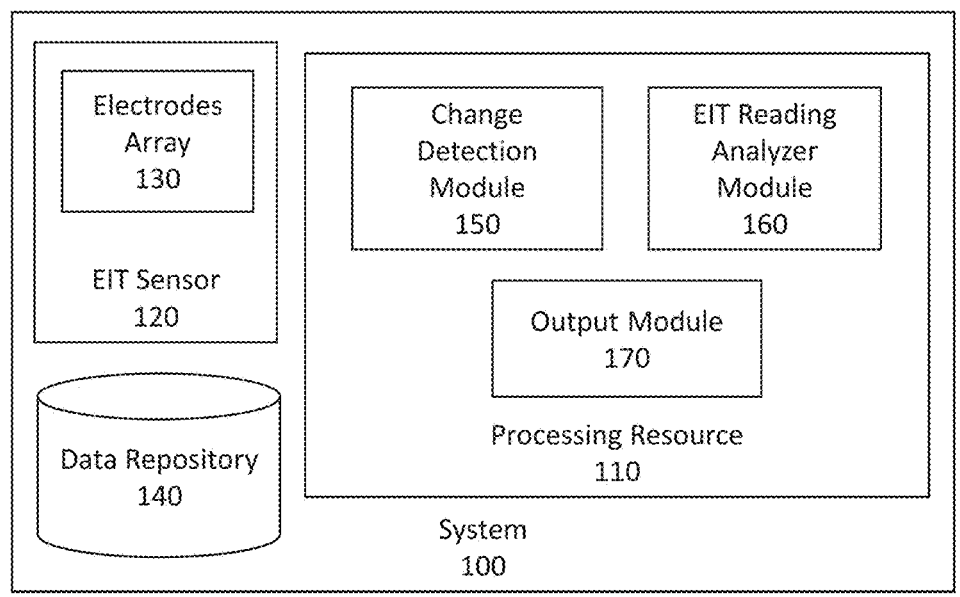
FIG. 1 is a block diagram schematically illustrating one example of a system for detecting changes in human tissues, in accordance with the presently disclosed subject matter.

In the following detailed description, numerous specific details are set forth in order to provide a thorough understanding of the presently disclosed subject matter. However, it will be understood by those skilled in the art that the presently disclosed subject matter may be practiced without these specific details. In other instances, well-known methods, procedures, and components have not been described in detail so as not to obscure the presently disclosed subject matter.

In the drawings and descriptions set forth, identical reference numerals indicate those components that are common to different embodiments or configurations.

Unless specifically stated otherwise, as apparent from the following discussions, it is appreciated that throughout the specification discussions utilizing terms such as "obtaining", "acquiring", "analyzing", "comparing", "providing", "repeating", "utilizing" or the like, include action and/or processes of a computer that manipulate and/or transform data into other data, said data represented as physical quantities, e.g. such as electronic quantities, and/or said data representing the physical objects. The terms "computer", "processor", and "controller" should be expansively construed to cover any kind of electronic device with data processing capabilities, including, by way of non-limiting example, a personal desktop/laptop computer, a server, a computing system, a communication device, a smartphone, a tablet computer, a smart television, a processor (e.g. digital signal processor (DSP), a microcontroller, a field programmable gate array (FPGA), an application specific integrated circuit (ASIC), etc.), a group of multiple physical machines sharing performance of various tasks, virtual servers co-residing on a single physical machine, any other electronic computing device, and/or any combination thereof.

The operations in accordance with the teachings herein may be performed by a computer specially constructed for the desired purposes or by a general-purpose computer specially configured for the desired purpose by a computer program stored in a non-transitory computer readable storage medium. The term "non-transitory" is used herein to exclude transitory, propagating signals, but to otherwise include any volatile or non-volatile computer memory technology suitable to the application.

As used herein, the phrase "for example," "such as", "for instance" and variants thereof describe non-limiting embodiments of the presently disclosed subject matter. Reference in the specification to "one case", "some cases", "other cases" or variants thereof means that a particular feature, structure or characteristic described in connection with the embodiment(s) is included in at least one embodiment of the presently disclosed subject matter. Thus, the appearance of the phrase "one case", "some cases", "other cases" or variants thereof does not necessarily refer to the same embodiment(s).

It is appreciated that, unless specifically stated otherwise, certain features of the presently disclosed subject matter, which are, for clarity, described in the context of separate embodiments, may also be provided in combination in a single embodiment. Conversely, various features of the presently disclosed subject matter, which are, for brevity, described in the context of a single embodiment, may also be provided separately or in any suitable sub-combination.

Figure 2:
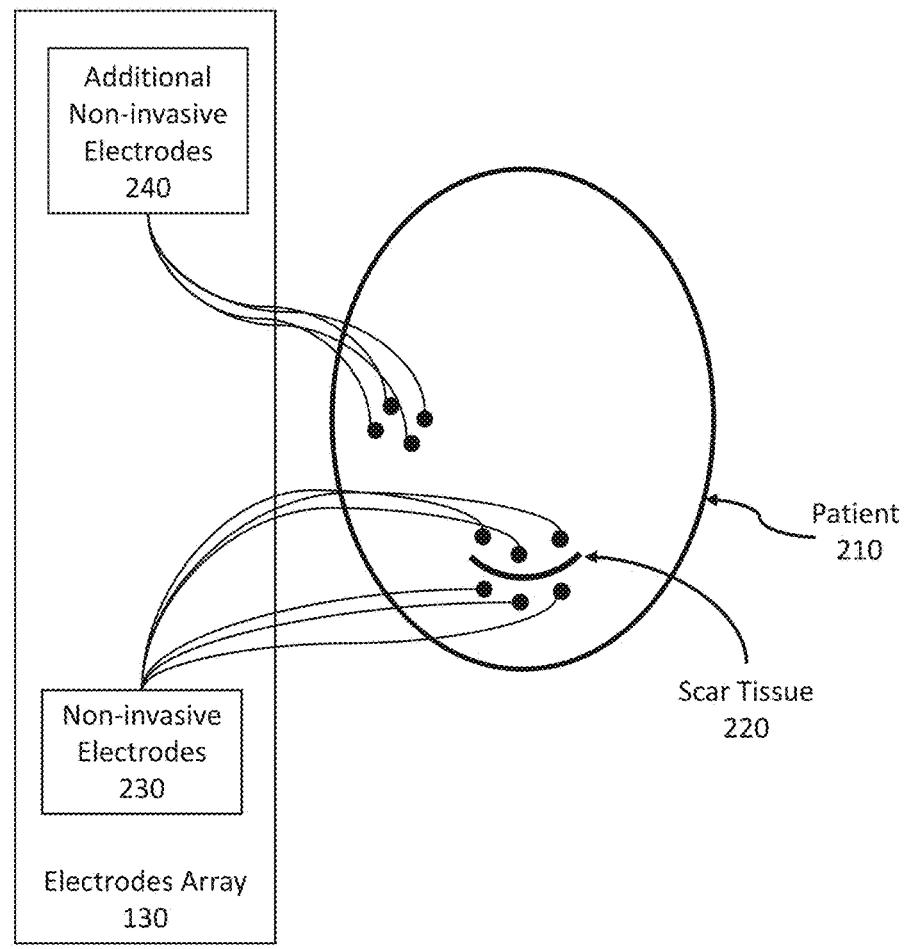
FIG. 2 is a schematic illustration of placement of electrodes of a system for detecting changes in human tissues, in accordance with the presently disclosed subject matter.
Figure 6:
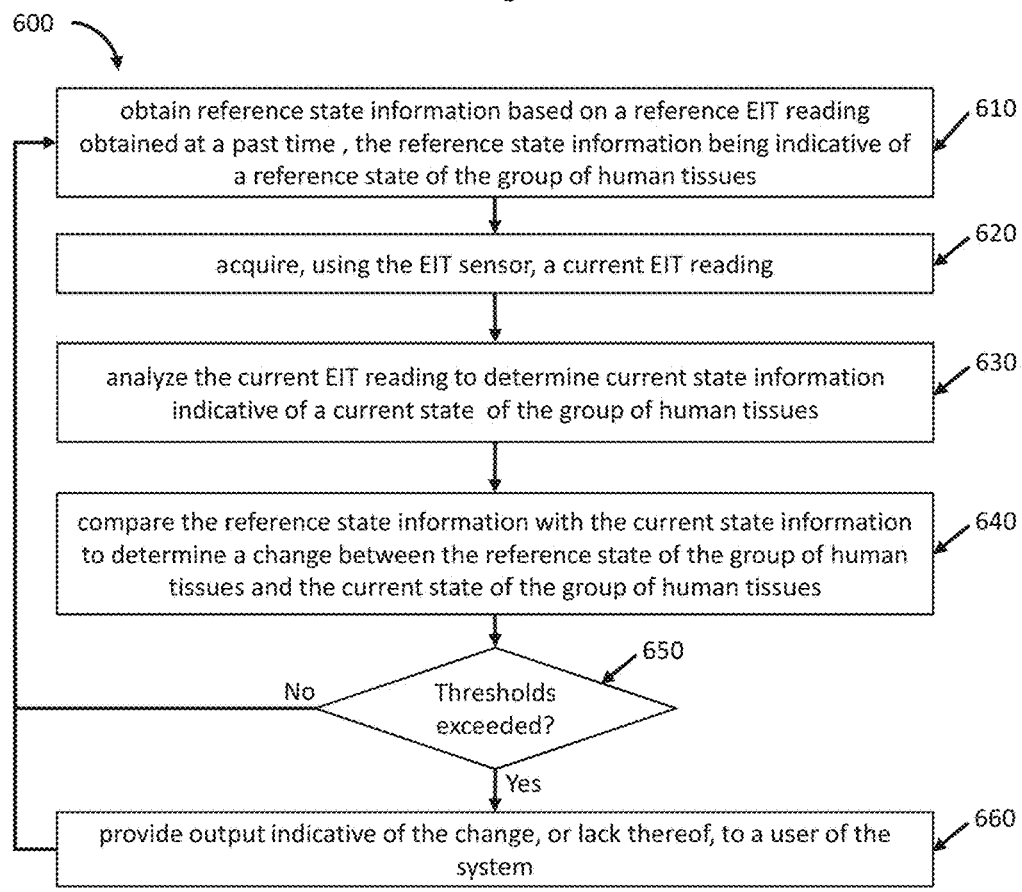
FIG. 6 is a flowchart illustrating one example of a sequence of operations carried out for detecting changes in human tissues, in accordance with the presently disclosed subject matter.
Figure 7:
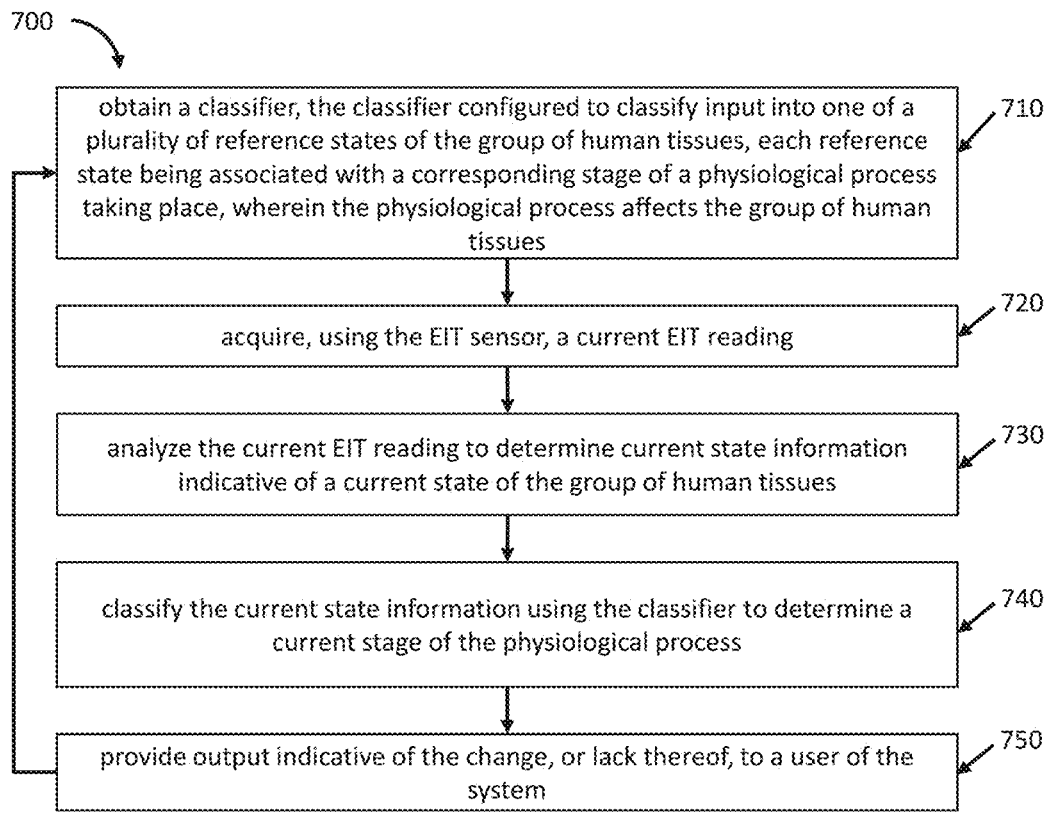
FIG. 7 is a flowchart illustrating another example of a sequence of operations carried out, for detecting changes in human tissues, in accordance with the presently disclosed subject matter.
Figure 8:
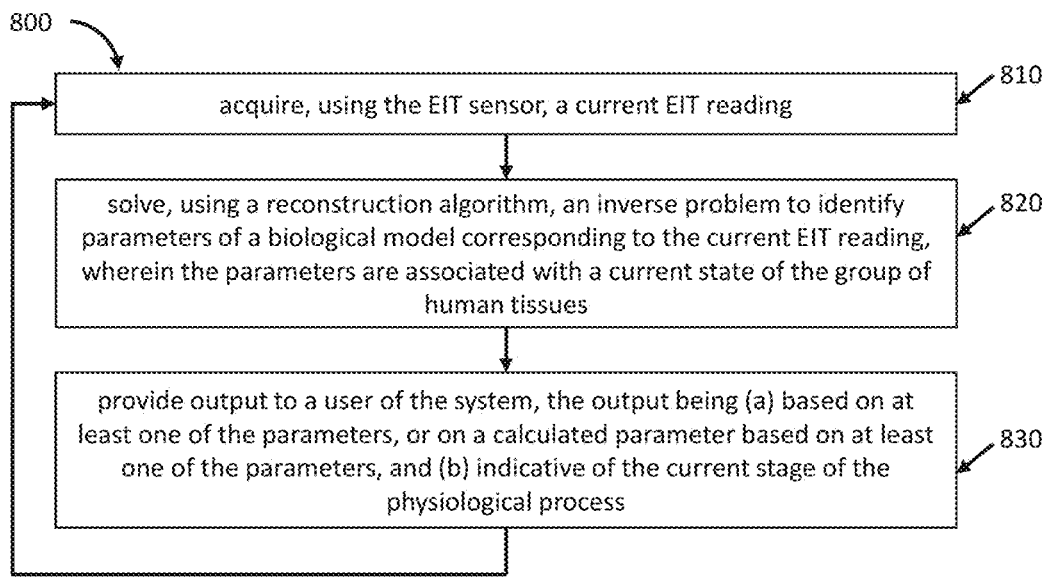
FIG. 8 is a flowchart illustrating yet another example of a sequence of operations carried out for detecting changes in human tissues, in accordance with the presently disclosed subject matter.

In embodiments of the presently disclosed subject matter, fewer, more and/or different stages than those shown in FIGS. 6-8 may be executed. In embodiments of the presently disclosed subject matter one or more stages illustrated in FIGS. 6-8 may be executed in a different order and/or one or more groups of stages may be executed simultaneously. FIGS. 1 and 2 illustrate a general schematic of the system architecture in accordance with an embodiment of the presently disclosed subject matter. Each module in FIG. 1 can be made up of any combination of software, hardware and/or firmware that performs the functions as defined and explained herein. Some of the modules in FIG. 1 may be centralized in one location or dispersed over more than one location. In other embodiments of the presently disclosed subject matter, the system may comprise fewer, more, and/or different modules than those shown in FIGS. 1 and 2.

Any reference in the specification to a method should be applied mutatis mutandis to a system capable of executing the method and should be applied mutatis mutandis to a non-transitory computer readable medium that stores instructions that once executed by a computer result in the execution of the method.

Any reference in the specification to a system should be applied mutatis mutandis to a method that may be executed by the system and should be applied mutatis mutandis to a non-transitory computer readable medium that stores instructions that may be executed by the system.

Any reference in the specification to a non-transitory computer readable medium should be applied mutatis mutandis to a system capable of executing the instructions stored in the non-transitory computer readable medium and should be applied mutatis mutandis to method that may be executed by a computer that reads the instructions stored in the non-transitory computer readable medium.

It is to be noted that although reference is made in the detailed description to human body/tissues, the presently disclosed subject matter is not thus limited and it can be applied to any other biological entities' body/tissue (including animals), as well as to monitoring fluid and/or gas flow in pipes, or heat transfer, mutatis mutandis.

Bearing this in mind, attention is drawn to FIG. 1, showing a block diagram schematically illustrating one example of a system for detecting changes in human tissues, in accordance with the presently disclosed subject matter.

According to the presently disclosed subject matter, system 100 comprises an EIT sensor 120. The EIT sensor 120 is configured to acquire readings associated with a group of human tissues of a patient, as further detailed herein. For this purpose, an electrode array 130 of the EIT sensor 120 is utilized. At least part of the electrodes of the electrode array 130 are configured to be placed, in a non-invasive manner, around an area of interest which includes the group of human tissues with which the readings are associated. The group of human tissues with which the readings are associated is confined by the boundaries formed by the placement of the electrodes around the area of interest, noting that the group of human tissues can be located on the skin surface of the patient's body, or under the skin surface of the patient's body. An illustration of an exemplary placement of the electrodes of the electrode array 130 is provided, and discussed in greater detail, with respect to FIG. 2. It is to be noted that in some cases, the electrodes can be implanted inside the patient's body, around the area of interest.

System 100 can further comprise a data repository 140 (e.g. a database, a storage system, a memory including Read Only Memory—ROM, Random Access Memory—RAM, or any other type of memory, etc.) configured to store data, including inter alia information of historical readings acquired by the EIT sensor 120 (optionally with metadata thereon, such as identification information identifying the person from which the readings were acquired, medical information associated with such person, etc.), information defining one or more sequences of projections to be made by the EIT sensor 120, information defining frequencies of electrical current to be transmitted by electrodes of the electrode array 130, information of one or more models describing evolution of physiological processes that can be associated with the group of body tissues (e.g. models describing evolution of a C-section scar rupture, or any other physiological process whose monitoring is desirable), a classifier capable of classifying input into one of a plurality of reference states of the group of human tissues (e.g. as shown by the models describing evolution of physiological processes, where each reference state is associated with a corresponding stage of a physiological process affecting the group of human tissues taking place), etc. Data repository 140 can be further configured to enable retrieval and/or update and/or deletion of the stored data. It is to be noted that in some cases, data repository 140 can be distributed between a plurality of locations, local and/or remotely accessible by the system 100 (e.g. via a wired/wireless connection).

System 100 further comprises a processing resource 110. processing resource 110 can be one or more processing units (e.g. central processing units), microprocessors, microcontrollers or any other computing devices or modules, including multiple and/or parallel and/or distributed processing units, which are adapted to independently or cooperatively process data for controlling relevant resources of the system 100 and for enabling operations related to resources of the system 100.

The processing resource 110 can comprise one or more of the following modules: change detection module 150, EIT reading analyzer module 160, and alert module 170.

According to some examples of the presently disclosed subject matter, change detection module 150 can be configured to detect changes in states of the group of human tissues, as further detailed herein, inter alia with reference to FIGS. 6-8. The EIT analyzer module 160 be configured to determine states of the group of human tissues by analyzing EIT readings associated with the group of human tissues. The output module 170 can be configured to provide output indicative of a change, or lack thereof, to a user of the system. In some cases, the output can include one or more alerts, e.g. when changes that require attention (e.g. of a medical practitioner) are detected. The output can be provided via a display, via speakers, via vibrating elements, or in any other manner that provides the required information to the relevant user of the system 100 (e.g. a medical practitioner, a patient, etc.).

Attention is drawn to FIG. 2, a schematic illustration of placement of electrodes of a system for detecting changes in human tissues, in accordance with the presently disclosed subject matter.

According to some examples of the presently disclosed subject matter, a group of at least four non-invasive electrodes 230 of the electrodes array 130 are attached to a body of a patient 210, around an area of interest. The area of interest in the depicted illustration is a scar tissue 220, such as a C-section scar of the patient 210. It is to be noted however that the area of interest can otherwise include transplanted skin, one or more teeth, one or more blood vessels, one or more parts of the brain, one or more bones, a lung or both lungs, or any other part of the human body which includes human tissues that, may change instantaneously, or over time.

In some cases, another group of at least four additional non-invasive electrodes 240 of the electrodes array 130 can be attached to the body of the patient 210 around another area that does not overlap to the area of interest. EIT readings acquired by such group of additional non-invasive electrodes 240 can be used as reference to the readings acquired by the at least four non-invasive electrodes 230. Looking at an example of a VBAC procedure, the at least four non-invasive electrodes 230 can be placed around the C-section scar, whereas the at least four additional non-invasive electrodes 240 can be placed around a non-scarred area. In such case, upon rupture of the C-section scar, the readings obtained by the at least four non-invasive electrodes 230 will indicate a change, whereas the readings obtained by the at least four additional non-invasive electrodes 240 that are farther away from the C-section scar will indicate a smaller change, if any (as the electrical potential change becomes smaller the farther the reading is obtained from the scar whose rupture caused such change). This can enable identification of scar rupture at a higher degree of certainty compared to a scenario where no additional non-invasive electrodes 240 are utilized, as further detailed herein, inter alia with reference to FIGS. 6-8.

Figure 3:
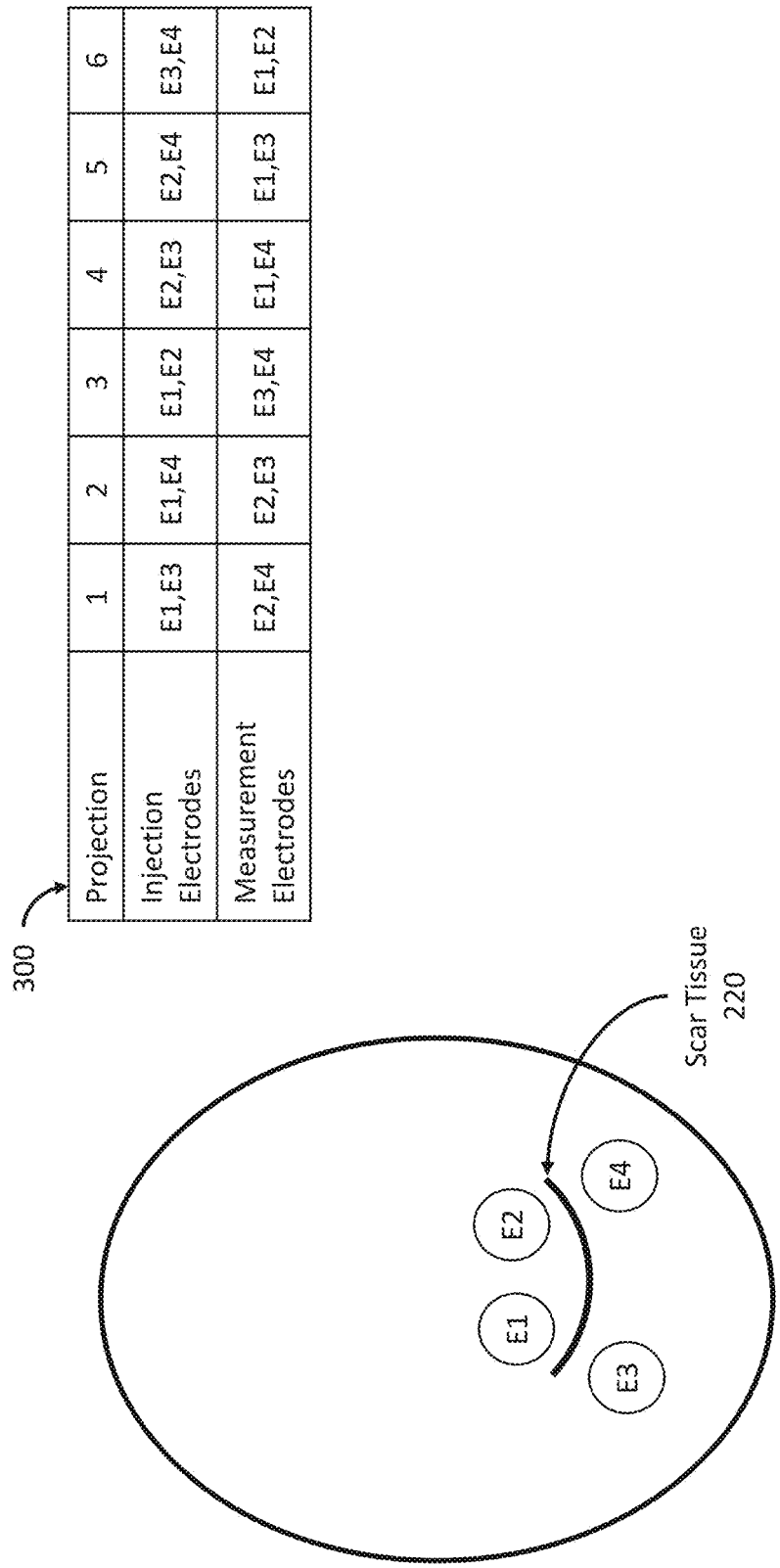
FIG. 3 is a schematic illustration of a sequence of projections performed by a system for detecting changes in human tissues, in accordance with the presently disclosed subject matter.

Having shown the placement of electrodes of the system 100, attention is drawn to FIG. 3, schematically illustrating a sequence of projections performed by a system for detecting changes in human tissues, in accordance with the presently disclosed subject matter.

An EIT reading is comprised of a sequence of projections made between pairs of electrodes. A single projection includes at least one pair of the non-invasive electrodes 230 transmitting electrical current from a first electrode of the pair to a second electrode of the pair, and at least one other pair of other non-invasive electrodes of the non-invasive electrodes 230 measuring an electrical potential between a first electrode of the other pair and a second electrode of the other pair simultaneously to the transmittal of the electrical current from the first electrode of the pair to the second electrode of the pair, wherein the and the other pair include different non-invasive electrodes at each projection of the series.

In the illustration, four non-invasive electrodes are shown (namely: E1, E2, E3 and E4), placed around an area of interest, which in the illustrated example is a scar tissue 220. In the illustrated scenario, six projections are made, as shown in the projections table 300:

1. E1 transmits/injects electrical current to E3, and E2 and E4 measure the electrical potential therebetween;
2. E1 transmits/injects electrical current to E4, and E2 and E3 measure the electrical potential therebetween;
3. E1 transmits/injects electrical current to E2, and E3 and E4 measure the electrical potential therebetween;
4. E2 transmits/injects electrical current to E3, and E1 and E4 measure the electrical potential therebetween;
5. E2 transmits/injects electrical current to E4, and E1 and E3 measure the electrical potential therebetween; and
6. E3 transmits/injects electrical current to E4, and E1 and E2 measure the electrical potential therebetween.

It is to be noted that when placing the non-invasive electrodes 230 around the area of interest comprising the group of human tissues whose change monitoring is desirable—the measured electrical potential is effected by at least part of such group of human tissues.

It is to be further noted that although in the illustrated example only four non-invasive electrodes 230 are shown, this is by no means limiting, and a larger number of non-invasive electrodes can be used, mutatis mutandis. When a larger number of non-invasive electrodes is used, one pair thereof can be used to transmit/inject electrical current therebetween, while a plurality of other pairs thereof can be used to measure the electrical potential therebetween as a result of the pair transmitting/injecting electrical current therebetween.

It is to be still further noted that although in the illustration no additional non-invasive electrodes 240 placed in an area other than the area of interest are shown, in some cases, at least four additional non-invasive electrodes 240 can be used, as detailed herein.

In some cases, the projections of the series are performed in synchronization with a breathing cycle of the patient. This enables reducing variance that result from differences in acquisition times of the measurements in each projection during the breathing cycle of the patient. In this respect, it, is to be appreciated that in some cases, the measurements acquired from a given group of human tissues when a patient is exhaling, may be different than the measurements acquired from the same given group of human tissues when the patient is inhaling, even if the given group of human tissues does not physically change. Additionally, or alternatively, each projection can be associated with information enabling determination of a phase of the breathing cycle at which it was acquired. Having this knowledge can enable dealing with variance that result from differences in acquisition times of the measurements in each projection during the breathing cycle of the patient.

Figure 4:
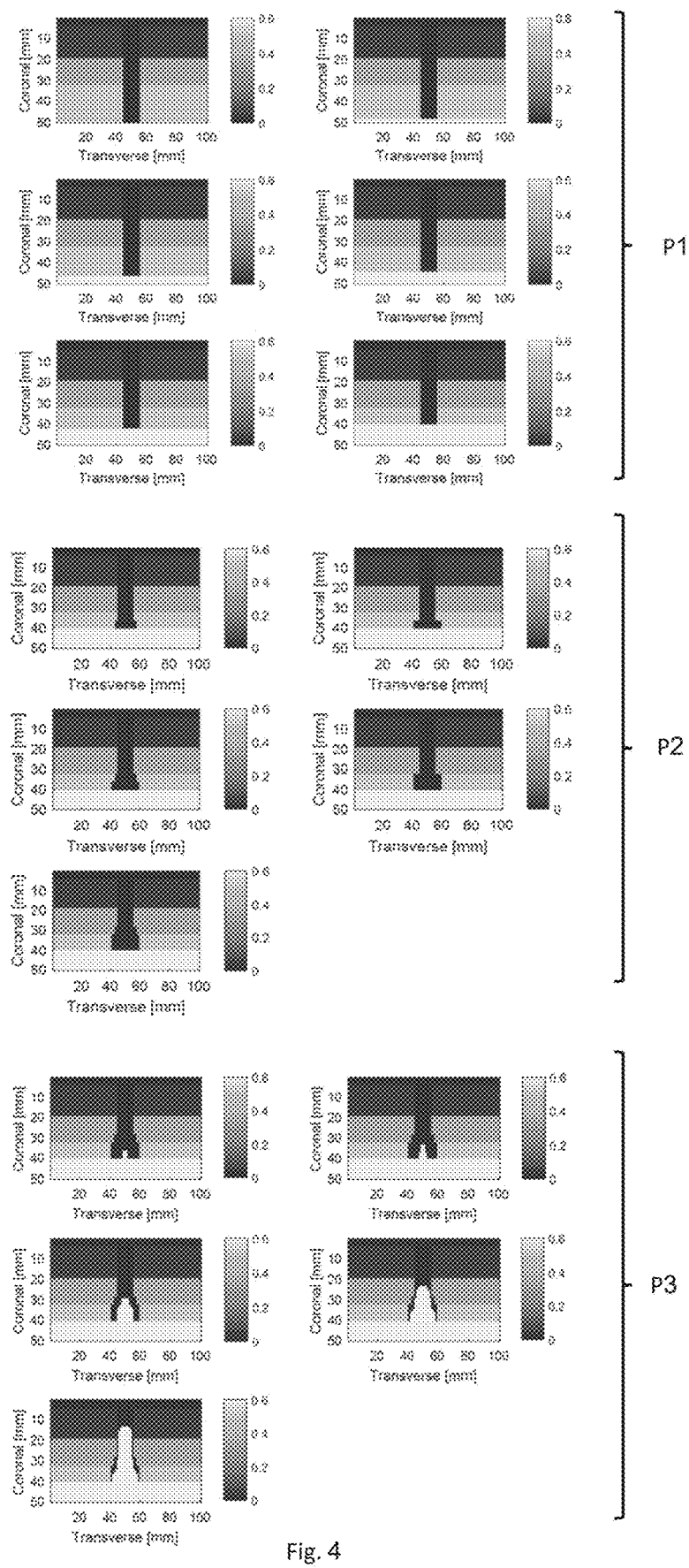
FIG. 4 is an illustration of evolution of a C-section scar rupture as detected by a system for detecting changes in human tissues, in accordance with the presently disclosed subject matter.

Although the system 100 can be used to identify changes in various types of human tissues, the presently disclosed subject matter can be useful in predicting C-section scar rupture. Turning to FIG. 4, there is shown an exemplary illustration of evolution of a C-section scar rupture as detected by a system for detecting changes in human tissues, in accordance with the presently disclosed subject matter.

In the non-limiting exemplary model shown in the illustration three phases are shown: P1, P2 and P3. P1 is indicative of evolution of tension on the C-section scar. At this phase, the scar geometry is not deformed, however, due to the development of the tension, the likelihood of the scar rupturing increases. P2 is indicative of evolution of scar geometry deformation, as the scar deformation increases, the likelihood of the scar rupturing increases. P3 is indicative of evolution of a scar rupture itself, in which fluid (e.g. blood, amniotic fluid, etc.) bursts through the ruptured scar. In other cases (not shown in the illustrated model), fluids do not immediately burst through the ruptured scar, but a gap filled with air is created by the scar rupturing, which also affects the measurements acquired using the non-invasive electrodes 230).

It is to be noted that having the ability to identify the current state of the scar, for identifying the likelihood of it rupturing, is critical, and it can enable saving lives during VBAC by providing indications of the likelihood of the scar rupturing during the VBAC, without the need of dedicated personnel or expensive equipment that is not always available during VBAC.

It is to be noted that ruptures can lave different characteristics in different scenarios, and in some cases, they can evolve differently than in the illustrated example.

Figure 5:
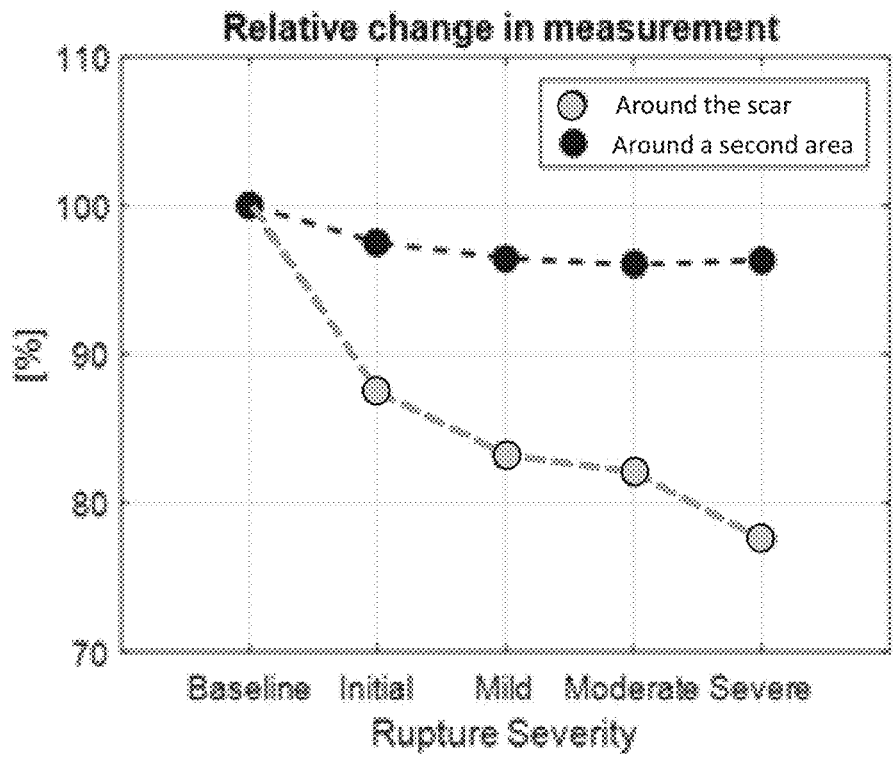
FIG. 5 is a diagram showing a relative change in measurements of a system for detecting changes in human tissues, when measurements are obtained from a first area near a C-section scar rupture and from a second area farther from the C-section scar rupture, in accordance with the presently disclosed subject matter.

As indicated herein, in some cases, EIT readings are obtained from at least four non-invasive electrodes 230 that are placed around an area of interest, and from at least four additional non-invasive electrodes 240 that are placed around another area that, does not overlap the area of interest. FIG. 5 is a diagram showing a relative change in measurements of a system for detecting changes in human tissues, when measurements are obtained from a first area near a C-section scar rupture and from a second area farther from the C-section scar rupture, in accordance with the presently disclosed subject matter.

The human body is always active. Humans breathe, their heart heats, they move, and each human body activity can affect the electrical potential measured by the non-invasive electrodes 230 and the additional non-invasive electrodes 240 of the electrode array 130 of the EIT sensor 120 of the system 100. Accordingly, it is desirable to differentiate between such normal changes of electrical potential and changes that result for example from tissue dissolution/separation, e.g. from scar rupture. Therefore, in some cases, the non-invasive electrodes 230 are placed around the area of interest (which includes the human body tissues whose change detection is desirable), while the additional non-invasive electrodes are placed around a second area, that does not overlap with the area of interest. Changes that affect both the area of interest and the second area are likely to occur due to normal body activity, while changes that occur in the area of interest that are not identical to the changes that occur in the second area, are likely to be a result of abnormal activity that is potentially hazardous.

In the diagram, two sequences of measurements are shown, one taken by the non-invasive electrodes 230 placed around the area of interest (e.g. a C-section scar), and the other by the additional non-invasive electrodes 240 placed around a second area that does not overlap with the area of interest, and is preferably at a distance that will result in the readings not being affected by changes that take place within the area of interest (e.g. the scar rupturing), or being less affected by such changes than the readings obtained from the non-invasive electrodes 230 placed around the area of interest. As can be seen, upon a scar rupturing, the readings obtained from the non-invasive electrodes 230 placed around the area of interest are substantially different than the readings that are obtained in parallel from the additional non-invasive electrodes 240 placed around the second area. While the changes between the readings obtained from the additional non-invasive electrodes 240 placed around the second area in the illustrated sequence of readings are less than 5%, the changes between the readings obtained from the non-invasive electrodes 230 placed around the area of interest are higher than 10%, and reach over 20% over time.

It is to be noted that the diagram is provided for illustrative purposes only, and it is by no means limiting. In addition, although reference is made to C-section scar rupturing in the illustrated example, this is by no means limiting, and other changes to other human tissues are contemplated as well, mutatis mutandis.

Attention is now drawn to FIG. 6, a flowchart illustrating one example of a sequence of operations carried out for detecting changes in human tissues, in accordance with the presently disclosed subject matter.

According to some examples of the presently disclosed subject matter, system 100 can be configured to perform a change detection process 600, e.g. utilizing the change detection module 150.

For this purpose, system 100 is configured to obtain reference state information based on at least one reference EIT reading obtained at a past time, the reference state information being indicative of a reference state of the group of human tissues (block 610). The reference state information can be an actual reading obtained by an EIT sensor (e.g. EIT sensor 120), or it can be any other information calculated based on such EIT reading, or on a plurality of EIT readings, such as a calculated parameter (e.g. obtained using mathematical/statistical operations on the plurality of EIT readings, or on sub-groups thereof), a conductivity map, or any other information that can be extracted from the EIT reading/s obtained at a past time, before acquiring a current EIT reading at block 620 herein.

One non-limiting example of a calculated parameter calculated based on the reference EIT reading can be obtained using the following formula:

$$R_t = \frac{\left(\sum_{i=1}^{N} y_{i,t}\right)}{I_{i,t}}$$

in which:
(a) $Y=\{y_1, y_2, \ldots, y_N\}$ is the reference EIT reading vector (for a specific time point t). The vector comprises N independent entries, each associated with a measurement obtained from a single projection from an applied sequence of projections (as detailed herein);
(b) $I_{i,t}$ is a scalar, representing the amplitude of the electrical current injected on the $i^{th}$ projection at a specific time point t; and
(c) $R_t$ is the effective resistance of an EIT reading at a specific time point t.

The calculated parameter ($R_t$) can be converted to conductivity using the following relation, in which $\sigma_t$ is the effective conductivity of a specific time point:

$$\sigma_t = \frac{1}{R_t}$$

It is to be noted, as detailed herein, that a single EIT reading obtained by an EIT sensor (e.g. EIT sensor 120 which comprises at least four non-invasive electrodes 230) includes a series of one or more subsequent projections, each of the projections obtained by: (a) at least one pair of the non-invasive electrodes (e.g. non-invasive electrodes 230) actively transmitting electrical current from a first electrode of the pair to a second electrode of the pair, and (b) at least one other pair of other non-invasive electrodes of the non-invasive electrodes (e.g. non-invasive electrodes 230) measuring an electrical potential between a first electrode of the other pair and a second electrode of the other pair simultaneously to the transmittal of electrical current by the first electrode of the pair to the second electrode of the pair, wherein the pair and the other pair include different non-invasive electrodes at each projection of the series. An illustration of the series of projection is provided herein with reference to FIG. 3.

Upon the non-invasive electrodes (e.g. non-invasive electrodes 230) being positioned around an area of interest comprising the group of human tissues of the patient whose change detection is desired, at least part of the measured electrical potential is affected by at least part of such group of human tissues.

The reference EIT reading/s based on which the reference state information is determined is obtained at a past time, while the past time can depend on the implementation: (A) For real-time monitoring, that is required for example when monitoring a state of a scar (e.g. a C-section scar), the reference EIT reading/s can be a reading/s obtained before the current EIT reading that is obtained at block 620 herein. In such cases, each current EIT, or some of the current EIT readings obtained at block 620, are later used as the reference state information (or as a basis based on which the reference state information is determined). (B) For non-real time monitoring, such as in cases when monitoring teeth for appearance of cavities (being a change in teeth, which are groups of human tissues), the reference EIT reading/s can be EIT reading/s that were obtained a certain time period before obtainment of the current EIT reading, such as one or more hours/days/weeks/months/years before obtainment of the current EIT reading at block 620.

It is to be noted that the reference state information is a time-based reference, in the sense that it is based on reference EIT reading/s acquired at a past time, before acquisition of the current EIT reading at block 620 herein. In this respect, it is to be noted that in some cases, the reference EIT reading/s can include, as part of the reading itself, a location-based reference. As indicated herein, in some cases, the EIT reading can be obtained from both (a) at least four non-invasive electrodes (e.g. non-invasive electrodes 230) placed around the area of interest (e.g. a C-section scar), and (b) at least four additional non-invasive electrodes (e.g. additional non-invasive electrodes 240) placed around a second area that does not overlap with the area of interest. In such cases, the part of the EIT reading that is obtained by the additional non-invasive electrodes (e.g. additional non-invasive electrodes 240) can be used as location-based reference, that can enable differentiating between normal changes that result from the body's regular activity, and abnormal changes that occur within the area of interest. In some cases, the location-based reference can also be used for reducing electrical noise.

Returning to the flowchart, system 100 is further configured to acquire, using the EIT sensor 120, a current EIT reading (block 620). The current EIT reading is obtained by the EIT sensor 120 (which comprises at least four non-invasive electrodes 230), and it includes a series of one or more subsequent projections, each of the projections obtained by: (a) at least one pair of the non-invasive electrodes 230 actively transmitting electrical current from a first electrode of the pair to a second electrode of the pair, and (b) at least one other pair of other non-invasive electrodes of the non-invasive electrodes 230 measuring an electrical potential between a first electrode of the other pair and a second electrode of the other pair simultaneously to the transmittal of electrical current by the first electrode of the pair to the second electrode of the pair, wherein the pair and the other pair include different non-invasive electrodes at each projection of the series. An illustration of the series of projection is provided herein with reference to FIG. 3. Upon the non-invasive electrodes 230 being positioned around an area of interest comprising the group of human tissues of the patient whose change detection is desired, at least part of the measured electrical potential (measured by the other pair of other non-invasive electrodes of the non-invasive electrodes 230) is affected by at least part of such group of human tissues.

In some cases, the series of one or more subsequent projections can be defined by a scheme, which can define, for each projection of the series, a frequency of the electrical current transmitted by each of the first electrodes to each of the second electrodes of each of the pairs of the non-invasive electrodes 230. In some cases, the frequency transmitted from a first electrode to a second electrode of a first pair of the pairs of the non-invasive electrodes 230 can be different than a frequency transmitted from a first electrode to a second electrode of a second pair of the pairs of the non-invasive electrodes 230. In some cases, the frequency transmitted from the first electrode to the second electrode of a given pair of the pairs in a first projection of the series is different than the frequency transmitted from the first electrode to the second electrode of the same given pair in a second projection of the series other than the first projection.

As indicated herein, in some cases, the projections of the series can be performed in synchronization with a breathing cycle of the patient. This enables reducing variance that result from differences in acquisition times of the measurements in each projection during the breathing cycle of the patient. In this respect, it is to be appreciated that in some cases, the measurements acquired from a given group of human tissues when a patient is exhaling, may be different than the measurements acquired from the same given group of human tissues when the patient is inhaling, even if the given group of human tissues does not physically change.

It is to be noted that the current EIT reading can include, as part of the reading itself, a location-based reference. As indicated herein, in some cases, the EIT reading can be obtained from both (a) at least four non-invasive electrodes 230 placed around the area of interest (e.g. a C-section scar), and (b) at least four additional non-invasive electrodes 240 placed around a second area that does not overlap with the area of interest (and therefore, the electrical potential measured therein is less affected by the group of human tissues whose change detection is desired, if it is at all affected thereby). In such cases, the part of the EIT reading that is obtained by the additional non-invasive electrodes 240 can be used as location-based reference, that can enable differentiating between normal changes that result from the body's regular activity, and abnormal changes that occur within the area of interest. In some cases, the location-based reference can also be used for reducing electrical noise.

System 100 can analyze the current EIT reading to determine current state information indicative of a current state of the group of human tissues (block 630). In some cases, the current state information can be the actual reading obtained by the EIT sensor 120, or it can be any other information calculated based on the current EIT reading, such as a calculated parameter, a conductivity map, or any other information that can be extracted from the current EIT reading.

One non-limiting example of a calculated parameter calculated based on the current EIT reading can be obtained using the following formula:

$$R_t = \frac{\left(\sum_{i=1}^{N} x_{i,t}\right)}{I_{i,t}}$$

in which:
(d) $X_t = \{x_1, x_2, \ldots, x_N\}$ is the current EIT reading vector (for a specific time point t). The vector comprises N independent entries, each associated with a measurement obtained from a single projection from an applied sequence of projections (as detailed herein);
(e) $1_{i,t}$ is a scalar, representing the amplitude of the electrical current injected on the $i^{th}$ projection at a specific time point t; and
(f) $R_t$ is the effective resistance of an EIT reading at a specific time point t.

The calculated parameter ($R_t$) can be converted to conductivity using the following relation, in which $\sigma_t$ is the effective conductivity of a specific time point:

$$\sigma_t = \frac{1}{R_t}$$

Having the reference state information obtained at block 610 and the current state information determined at block 630, the system 100 can compare the reference state information with the current state information to determine a change between the reference state of the group of human tissues and the current state of the group of human tissues (block 640).

One non-limiting example of a change determination, using the reference EIT reading as the reference state information and the current EIT reading as the current state information, can be made using the following formula, in which $X_t = \{x_1, x_2, \ldots, x_N\}$ and $Y = \{y_1, y_2, \ldots, y_N\}$ are the current EIT readings (for a specific time point t) and reference EIT readings vectors respectively. Both vectors comprise N independent entries, each associated with a measurement obtained from a single projection from an applied sequence of projections (as detailed herein), and $E_t$ is the current measure of the error between vectors $X_t$ and $Y$.

$$E_t = \|X_t - Y\|^2 = \sqrt{\sum_{i=1}^{N} (x_{i,t} - y_i)^2}$$

While monitoring a change to the group of human tissues (e.g. during labor of a pregnant woman), the error is calculated repeatedly, each time for the current EIT reading, and compared to a predefined threshold as detailed herein with reference to block 650. When the error exceeds the threshold, system 100 can provide an indication a clinically significant change.

in some cases, system 100 can be configured to check if the change between the reference state and the current state of the group of human tissues whose change detection is desired exceeds any pre-determined thresholds (block 650). It is to be noted that in some cases, some level of change may be permitted, as not every change is indicative of any risk to the patient. For example, when referring to a C-section scar, the scar may be under tension, which may cause it to change in a manner that does not pose a threat. However, when the change exceeds a threshold, it may be indicative that the likelihood of the scar rupturing justifies providing relevant output to a medical practitioner.

It is to be further noted that in some cases a plurality of thresholds may exist, each being associated with a respective likelihood of the scar rupturing, and each being associated with a respective output identifiable by a medical practitioner. For example, a first threshold may be indicative of a mild risk of a C-section scar to rupture, while a second threshold may be indicative of a high risk of the C-section scar to rupture. Upon none of the thresholds being met, a green light may be turned on as output indicating that the C-section scar is not at risk of rupturing, or at a low risk of rupturing. Upon the first threshold being met, a yellow light may be turned on as output indicating that the C-section scar is at a medium risk of rupturing. Upon the second threshold being met, a red light may be turned on as output indicating that the C-section scar is at a high risk of rupturing.

Upon any change level threshold being exceeded, system 100 can provide output indicative of the change to a user of the system (block 660). The output can include any one or any combination of two or more of the following output types: visual output provided via a display (e.g. a visual map of an area comprising the group of tissues) and/or a lighting system comprising one or more lights (which can optionally have different colors), sound output provided via one or more speakers, vibration output provided by one or more vibrating elements that can generate vibrations that can be sensed by a medical practitioner (or any other user of the system 100), or any other type of output that can enable a medical practitioner (or any other user of the system 100) to become aware of the output. It is to be noted that the output mechanisms may be part of the system 100, or they can be external thereto, while system 100 being operable to provide instructions thereto for causing it to provide the desired output.

It is to be noted that in some cases, output is provided to the user of the system 100 irrespective of any thresholds being breached, and also in cases where no change is detected whatsoever. In some implementations, lack of change can be indicative of a problematic situation, such as when checking transplanted skin acceptance by the body in which it is transplanted, or recovery of a scar/wound/bone fracture/brain damage/blood vessels. When no change is detected, it may be indicative of the body rejecting the transplanted skin or the scar/wound/bone fracture/brain damage/blood vessels not healing, and an alert of such lack of change may be required.

Whether output is provided to the user of system 100 or not, the process 600 can repeat itself, in real time (e.g. during labor of a patient having a C-section scar whose change detection is desirable), or periodically at different times (e.g. daily/weekly/monthly/yearly or any other time period, whether constant or variable). In some cases, in subsequent iterations of the process, the current state information that is determined at block 630 is being obtained by the system 100 as the reference state information of block 610, or as part thereof.

It is to be noted, that in a given embodiment, the group of human tissues whose change detection is desirable comprise a C-section scar, the change whose detection is desirable is deformation of the C-section scar, and the output includes an alert when based on the deformation of the scar, the likelihood of the scar to rupture is above a first threshold, and optionally a second alert, when based on the deformation of the scar, the likelihood of the scar to rupture is above a second threshold, higher than the first threshold.

It is to be noted that, with reference to FIG. 6, some of the blocks can be integrated into a consolidated block or can be broken down to a few blocks and/or other blocks may be added. Furthermore, in some cases, the blocks can be performed in a different order than described herein (for example, blocks 320 and 330 can be performed before block 310, block 360 can be performed before block 350, etc.). It is to be further noted that some of the blocks are optional. It should be also noted that whilst the flow diagram is described also with reference to the system elements that realizes them, this is by no means binding, and the blocks can be performed by elements other than those described herein.

Attention is now drawn to FIG. 7, a flowchart illustrating another example of a sequence of operations carried out for detecting changes in human tissues, in accordance with the presently disclosed subject matter.

According to some examples of the presently disclosed subject matter, system 100 can be configured to perform a change detection process 700, e.g. utilizing the change detection module 150.

For this purpose, system 100 is configured to obtain a classifier, the classifier configured to classify input (such as current state information indicative of a current state of the group of human tissues) into one of a plurality of reference states of the group of human tissues, each reference state being associated with a corresponding stage of a physiological process affecting the group of human tissues taking place (block 710).

The classifier can be based on models (e.g. the models stored on data repository 140), while the models can be based on real reference EIT readings obtained in the past (during previous labors of a given patient or other patients) and/or on simulated EIT readings obtained from a simulated patient (noting that the simulated patient can optionally be simulated using imaging modalities (such as MRI, CT, etc.) obtained from a specific patient so that the simulated patient can be based on the specific patient's anatomy). The models classify the real or simulated reference EIT readings obtained in the past according to the stage of the physiological process (e.g. scar rupture) that they represent.

In some cases, the classifier can be a machine learning classifier generated by performing machine learning on a training set of pre-classified EIT readings (being real and/or simulated EIT readings that are classified according to the stage of the physiological process (e.g. scar rupture) that they represent).

When using simulated EIT readings as detailed herein, one way to simulate the EIT readings is to use a computerized biological model. Such a model takes under consideration the physical mechanisms involved during the injection of an electrical current to a given volume conductor (in our case, a human geometry) and simulates the electrical potential values associated with a given injection for each voxel of a 3D geometry. One non limiting example of such model was introduced by Santosa and Vogelius that described the "direct current electrostatic problem" in a mathematical model and suggested a designated reconstruction algorithm to solve it (see Santosa, F. (1990). A backprojection algorithm for electrical impedance imaging, 50 (1), 216-243, which is incorporated herein by reference). Such a model can therefore be used to simulate a series of electrical current injections (i.e. an injection scheme) such that, for each injection, the difference between the potential values of the pair of the measuring electrodes will be calculated to produce a single simulated EIT reading.

System 100 is further configured to acquire, using the EIT sensor, a current EIT reading (block 720), as detailed with respect to block 620 of FIG. 6. System 100 can be configured to analyze the current EIT reading to determine current state information indicative of a current state of the group of human tissues (block 730), as detailed with respect to block 630 of FIG. 6.

System 100 can then classify the current state information, using the classifier obtained at block 710, to determine a current stage of the physiological process (block 740).

Based on the results of the classification, system 100 can provide output indicative of the change, or lack thereof, in comparison to a known previous stage of the physiological process, to a user of the system (block 750).

Whether output is provided to the user of system 100 or not, the process 700 can repeat itself, in real time (e.g. during labor of a patient having a C-section scar whose change detection is desirable), or periodically at different times (e.g. daily/weekly/monthly/yearly or any other time period, whether constant or variable).

It is to be noted that, with reference to FIG. 7, some of the blocks can be integrated into a consolidated block or can be broken down to a few blocks and/or other blocks may be added. Furthermore, in some cases, the blocks can be performed in a different order than described herein (for example, blocks 720 can be performed before block 710). It is to be further noted that some of the blocks are optional. It should be also noted that whilst the flow diagram is described also with reference to the system elements that realizes them, this is by no means binding, and the blocks can be performed by elements other than those described herein.

Attention is now drawn to FIG. 8, a flowchart illustrating yet another example of a sequence of operations carried out for detecting changes in human tissues, in accordance with the presently disclosed subject matter.

According to some examples of the presently disclosed subject matter, system 100 can be configured to perform a change detection process 800, e.g. utilizing the change detection module 150.

For this purpose, system 100 is configured to acquire, using the EIT sensor, a current EIT reading (block 810), as detailed with respect to block 620 of FIG. 6.

System 100 is further configured to solve, using a reconstruction algorithm, an inverse problem to identify parameters of a biological model corresponding to the current EIT reading, wherein the parameters are associated with a current state of the group of human tissues (block 820). The parameters can be geometrical parameters (relating to thickness, depth, etc.) that represent the size dimensions e.g. of a uterus or its surrounding, or a C-section scar thereon, etc. For this purpose, system 100 iteratively simulates reference EIT readings, by guessing at least some parameters of a computerized biological model associated with such simulated reference EIT readings, until it identifies a simulated reference EIT reading associated with a biological model having parameters that are within a threshold distance from the parameters that are associated with a current state of the group of human tissues, as inferred from the current EIT reading obtained at block 810. The biological model that resulted in parameters within a threshold distance from the parameters that are associated with a current state of the group of human tissues, is indicative of the current stage of the physiological process.

The computerized biological model takes under consideration the physical mechanisms involved during the injection of an electrical current to a given volume conductor (in our case, a human geometry) and simulates the electrical potential values associated with a given injection for each voxel of a 3D geometry. One non limiting example of such model was introduced by Santosa and Vogelius that described the "direct current electrostatic problem" in a mathematical model and suggested a designated reconstruction algorithm to solve it (see Santosa, F. (1990). A backprojection algorithm for electrical impedance imaging, 50 (1), 216-243, which is incorporated herein by reference). Such a model can therefore be used to simulate a series of electrical current injections (i.e. an injection scheme) such that, for each injection, the difference between the potential values of the pair of the measuring electrodes will be calculated to produce a single simulated EIT reading.

System 100 can provide output to a user of the system (block 830). The output provided by the system 100 is based on at least one of the parameters identified at block 820, or on a calculated parameter calculated based on at least one of the parameters identified at block 820 (e.g. a parameter calculated using the formula detailed with reference to block 640 herein). The output provided by the system 100 is indicative of the current stage of the physiological process.

Whether output is provided to the user of system 100 or not, the process 800 can repeat itself, in real time (e.g. during labor of a patient having a C-section scar whose change detection is desirable), or periodically at different times (e.g. daily/weekly/monthly/yearly or any other time period, whether constant or variable).

It is to be noted that, with reference to FIG. 8, some of the blocks can be integrated into a consolidated block or can be broken down to a few blocks and/or other blocks may be added. It is to be further noted that some of the blocks are optional. It should be also noted that whilst the flow diagram is described also with reference to the system elements that realizes them, this is by no means binding, and the blocks can be performed by elements other than those described herein.

It is to be understood that the presently disclosed subject matter is not limited in its application to the details set forth in the description contained herein or illustrated in the drawings. The presently disclosed subject matter is capable of other embodiments and of being practiced and carried out in various ways. Hence, it is to be understood that the phraseology and terminology employed herein are for the purpose of description and should not be regarded as limiting. As such, those skilled in the art will appreciate that the conception upon which this disclosure is based may readily be utilized as a basis for designing other structures, methods, and systems for carrying out the several purposes of the present presently disclosed subject matter.

It will also be understood that the system according to the presently disclosed subject matter can be implemented, at least partly, as a suitably programmed computer. Likewise, the presently disclosed subject matter contemplates a computer program being readable by a computer for executing the disclosed method. The presently disclosed subject matter further contemplates a machine-readable memory tangibly embodying a program of instructions executable by the machine for executing the disclosed method.

The invention claimed is:

1. A system for non-invasively detecting changes in human tissues, the system comprising:
   an Electrical Impedance Tomography (EIT) sensor capable of acquiring readings associated with a group of human tissues of a patient; and
   a processing resource configured to:
   (a) obtain reference state information based on a reference EIT reading obtained at a past time, the reference state information being indicative of a reference state of the group of human tissues;
   (b) acquire, using the EIT sensor, a current EIT reading;
   (c) analyze the current EIT reading to determine current state information indicative of a current state of the group of human tissues;
   (d) compare the reference state information with the current state information to determine a change between the reference state of the group of human tissues and the current state of the group of human tissues; and
   (e) provide output indicative of the change, or lack thereof, to a user of the system;
   wherein: (a) the EIT sensor comprises at least four non-invasive electrodes and at least four additional non-invasive electrodes, (b) the current EIT reading includes a series of one or more subsequent projections, each of the projections obtained by: (i) at least one pair of the non-invasive electrodes transmitting electrical current from a first electrode of the pair to a second electrode of the pair, and at least one other pair of other non-invasive electrodes of the non-invasive electrodes measuring an electrical potential between a first electrode of the other pair and a second electrode of the other pair simultaneously to the transmitting, wherein the pair and the other pair include different non-invasive electrodes at each projection of the series, and (ii) at least one third pair of the additional non-invasive electrodes transmitting electrical current from a first electrode of the third pair to a second electrode of the third pair, and at least one fourth pair of other additional non-invasive electrodes of the additional non-invasive electrodes measuring a second electrical potential between a first electrode of the fourth pair and a second electrode of the fourth pair simultaneously to the transmitting, wherein the third pair and the fourth pair include different additional non-invasive electrodes at each projection of the series, (c) the projections are obtained while the non-invasive electrodes are positioned around an area of interest comprising the group of human tissues of the patient, so that at least part of the measured electrical potential is affected by at least part of the group of human tissues, and while the additional non-invasive electrodes are positioned around another area that does not overlap to the area of interest, so that the second electrical potential measured is at least less affected by the group of human tissues and (d) the analysis of the current EIT reading includes utilizing the projections obtained by the additional non-invasive electrodes to differentiate between normal changes that result from routine activity of the patient's body, and abnormal changes that occur within the area of interest.

2. The system of claim 1, wherein the projections of the series are performed in synchronization with a breathing cycle of the patient.

3. The system of claim 1, wherein the group of human tissues is a cesarean section scar, the change is a deformation of the scar, and the output includes an alert when based on the deformation of the scar the likelihood of the scar to rupture is above a first threshold.

4. The system of claim 1, wherein the processing resource is further configured to iteratively repeat steps (a)-(e) at a plurality of different times, wherein at each given iteration of the iterations the reference state information is the current state information of one or more previous iterations performed before the given iteration.

5. The system of claim 3, wherein the processing resource is further configured to provide a second alert indicative of the change to the user of the system when based on the deformation of the scar the likelihood of the scar to rupture is above a second threshold, higher than the first threshold.

6. The system of claim 1, wherein at least one of the reference state information or the current state information is a calculated parameter, calculated utilizing the reference EIT reading or the current EIT reading, respectively.

7. The system of claim 1, wherein at least one of the reference state information or the current state information is the reference EIT reading itself or the current EIT reading itself, respectively.

8. The system of claim 1, wherein the series is defined by a scheme, and wherein the scheme further defines, for each projection of the series, a frequency of the electrical current transmitted by each of the first electrodes to each of the second electrodes of each of the pairs.

9. The system of claim 1, wherein the analysis includes utilizing the second electrical potential that is at least less affected by the group of human tissues for filtering noise from the at least part of the electrical potential that is affected by at least part of the group of human tissues.

10. A method for non-invasively detecting changes in human tissues, the method comprising:
   (a) obtaining reference state information based on a reference Electrical Impedance Tomography (EIT) reading obtained at a past time, the reference state information being indicative of a reference state of a group of human tissues of a patient;
   (b) acquiring, using an EIT sensor capable of acquiring readings associated with the group of human tissues, a current EIT reading;
   (c) analyzing the current EIT reading to determine current state information indicative of a current state of the group of human tissues;
   (d) comparing the reference state information with the current state information to determine a change between the reference state of the group of human tissues and the current state of the group of human tissues; and
   (e) providing output indicative of the change, or lack thereof, to a user;
   wherein: (a) the EIT sensor comprises at least four non-invasive electrodes and at least four additional non-invasive electrodes, (b) the current EIT reading includes a series of one or more subsequent projections, each of the projections obtained by: (i) at least one pair of the non-invasive electrodes transmitting electrical current from a first electrode of the pair to a second electrode of the pair, and at least one other pair of other non-invasive electrodes of the non-invasive electrodes measuring an electrical potential between a first electrode of the other pair and a second electrode of the other pair simultaneously to the transmitting, wherein the pair and the other pair include different non-invasive electrodes at each projection of the series, and (ii) at least one third pair of the additional non-invasive electrodes transmitting electrical current from a first electrode of the third pair to a second electrode of the third pair, and at least one fourth pair of other additional non-invasive electrodes of the additional non-invasive electrodes measuring a second electrical potential between a first electrode of the fourth pair and a second electrode of the fourth pair simultaneously to the transmitting, wherein the third pair and the fourth pair include different additional non-invasive electrodes at each projection of the series, (c) the projections are obtained while the non-invasive electrodes are positioned around an area of interest comprising the group of human tissues of the patient, so that at least part of the measured electrical potential is affected by at least part of the group of human tissues, and while the additional non-invasive electrodes are positioned around another area that does not overlap to the area of interest, so that the second electrical potential measured is at least less affected by the group of human tissues and (d) the analysis of the current EIT reading includes utilizing the projections obtained by the additional non-invasive electrodes to differentiate between normal changes that result from routine activity of the patient's body, and abnormal changes that occur within the area of interest.

11. The method of claim 10, wherein the projections of the series are performed in synchronization with a breathing cycle of the patient.

12. The method of claim 10, wherein the group of human tissues is a cesarean section scar, the change is a deformation of the scar, and the output includes an alert when based on the deformation of the scar the likelihood of the scar to rupture is above a first threshold.

13. The method of claim 10, further comprising iteratively repeating steps (a)-(e) at a plurality of different times, wherein at each given iteration of the iterations the reference state information is the current state information of one or more previous iterations performed before the given iteration.

14. The method of claim 12, further comprising providing a second alert indicative of the change to the user when based on the deformation of the scar the likelihood of the scar to rupture is above a second threshold, higher than the first threshold.

15. The method of claim 10, wherein at least one of the reference state information or the current state information is a calculated parameter, calculated utilizing the reference EIT reading or the current EIT reading, respectively.

16. The method of claim 10, wherein at least one of the reference state information or the current state information is the reference EIT reading itself or the current EIT reading itself, respectively.

17. The method of claim 10, wherein the series is defined by a scheme, and wherein the scheme further defines, for each projection of the series, a frequency of the electrical current transmitted by each of the first electrodes to each of the second electrodes of each of the pairs.

18. The method of claim 17, wherein the frequency transmitted from the first electrode to the second electrode of a given pair of the pairs in a first projection of the series is different than the frequency transmitted from the first electrode to the second electrode of the given pair in a second projection of the series other than the first projection.

19. The method of claim 10, wherein the analyzing includes utilizing the second electrical potential that is at least less affected by the group of human tissues for filtering noise from the at least part of the electrical potential that is affected by at least part of the group of human tissues.

20. A non-transitory computer readable storage medium having computer readable program code embodied therewith, the computer readable program code, executable by a processing resource of a computer to perform a method for non-invasively detecting changes in human tissues, the method comprising:
  (a) obtaining reference state information based on a reference Electrical Impedance Tomography (EIT) reading obtained at a past time, the reference state information being indicative of a reference state of a group of human tissues of a patient;
  (b) acquiring, using an EIT sensor capable of acquiring readings associated with the group of human tissues, a current EIT reading;
  (c) analyzing the current EIT reading to determine current state information indicative of a current state of the group of human tissues;
  (d) comparing the reference state information with the current state information to determine a change between the reference state of the group of human tissues and the current state of the group of human tissues; and
  (e) providing output indicative of the change, or lack thereof, to a user;
  wherein: (a) the EIT sensor comprises at least four non-invasive electrodes and at least four additional non-invasive electrodes, (b) the current EIT reading includes a series of one or more subsequent projections, each of the projections obtained by: (i) at least one pair of the non-invasive electrodes transmitting electrical current from a first electrode of the pair to a second electrode of the pair, and at least one other pair of other non-invasive electrodes of the non-invasive electrodes measuring an electrical potential between a first electrode of the other pair and a second electrode of the other pair simultaneously to the transmitting, wherein the pair and the other pair include different non-invasive electrodes at each projection of the series, and (ii) at least one third pair of the additional non-invasive electrodes transmitting electrical current from a first electrode of the third pair to a second electrode of the third pair, and at least one fourth pair of other additional non-invasive electrodes of the additional non-invasive electrodes measuring a second electrical potential between a first electrode of the fourth pair and a second electrode of the fourth pair simultaneously to the transmitting, wherein the third pair and the fourth pair include different additional non-invasive electrodes at each projection of the series, (c) the projections are obtained while the non-invasive electrodes are positioned around an area of interest comprising the group of human tissues of the patient, so that at least part of the measured electrical potential is affected by at least part of the group of human tissues, and while the additional non-invasive electrodes are positioned around another area that does not overlap to the area of interest, so that the second electrical potential measured is at least less affected by the group of human tissues and (d) the analysis of the current EIT reading includes utilizing the projections obtained by the additional non-invasive electrodes to differentiate between normal changes that result from routine activity of the patient's body, and abnormal changes that occur within the area of interest.

* * * * *